(12) United States Patent
Ghose et al.

(10) Patent No.: US 11,883,176 B2
(45) Date of Patent: Jan. 30, 2024

(54) LOW-POWER WEARABLE SMART ECG PATCH WITH ON-BOARD ANALYTICS

(71) Applicant: The Research Foundation for The State University of New York, Binghamton, NY (US)

(72) Inventors: Kanad Ghose, Vestal, NY (US); Sandeep S. Mittal, Wilkes Barre, PA (US)

(73) Assignee: The Research Foundation for The State University of New York

( * ) Notice: Subject to any disclaimer, the term of this patent is extended or adjusted under 35 U.S.C. 154(b) by 329 days.

(21) Appl. No.: 17/333,865

(22) Filed: May 28, 2021

(65) Prior Publication Data

US 2021/0369173 A1    Dec. 2, 2021

Related U.S. Application Data

(60) Provisional application No. 63/032,506, filed on May 29, 2020.

(51) Int. Cl.
| | |
|---|---|
| H04B 1/04 | (2006.01) |
| A61B 5/332 | (2021.01) |
| A61B 5/0245 | (2006.01) |
| A61B 5/00 | (2006.01) |
| A61B 5/024 | (2006.01) |

(Continued)

(52) U.S. Cl.
CPC ............ *A61B 5/332* (2021.01); *A61B 5/0006* (2013.01); *A61B 5/0245* (2013.01); *A61B 5/02405* (2013.01); *A61B 5/257* (2021.01); *A61B 5/282* (2021.01); *A61B 5/333* (2021.01); *A61B 5/352* (2021.01); *A61B 5/7203* (2013.01);

(Continued)

(58) Field of Classification Search
CPC ......... A61B 5/332; A61B 5/282; A61B 5/352; A61B 5/333; A61B 5/0006; A61B 5/257; A61B 5/02405; A61B 5/0245; A61B 5/7203; A61B 5/7217; A61B 5/7221; A61B 5/742; A61B 5/746; A61B 2560/0209

See application file for complete search history.

(56) References Cited

U.S. PATENT DOCUMENTS

| | | |
|---|---|---|
| 5,582,574 A | 12/1996 | Cramer |
| 5,658,277 A | 8/1997 | Marshall et al. |

(Continued)

*Primary Examiner* — Nhan T Le
(74) *Attorney, Agent, or Firm* — Hoffberg & Associates; Steven M. Hoffberg

(57) ABSTRACT

A wearable self-contained Smart ECG Sensor Patch (SEP) is provided for acquiring, analyzing and transmitting ECG data, heart rate and heart rate variability (heart rate variability) parameters to a host device via a secure Bluetooth low energy link. SEP incorporates all circuitry for acquisition, analysis and communication, and a battery on a small flexible substrate with two gold electrodes on the reverse side. Prior to on-board analysis, noise and motion artifacts are detected and ignored. SEP has been validated with archived ECG signals and testing on human subjects. The continuous acquisition and unique on-board analytics permit SEP to be used for prolonged monitoring scenarios with automatic alarm generations. SEP's aggressive power management techniques enable it to operate on a single coin battery for up to 250 hours. SEP suppresses transmissions of artifact data, which reduces power consumption.

22 Claims, 12 Drawing Sheets

(51) Int. Cl.
    *A61B 5/333*   (2021.01)
    *A61B 5/352*   (2021.01)
    *A61B 5/257*   (2021.01)
    *A61B 5/282*   (2021.01)

(52) U.S. Cl.
    CPC ............ *A61B 5/7221* (2013.01); *A61B 5/746* (2013.01); *A61B 2560/0209* (2013.01)

(56) References Cited

U.S. PATENT DOCUMENTS

| | | | |
|---|---|---|---|
| 5,669,391 A * | 9/1997 | Williams | A61N 1/37211 600/510 |
| 5,916,157 A | 6/1999 | Crosz, Jr. | |
| 6,327,795 B1 | 12/2001 | Russell | |
| 6,615,074 B2 | 9/2003 | Mickle et al. | |
| 6,842,999 B2 | 1/2005 | Russell | |
| 7,010,352 B2 | 3/2006 | Hogan | |
| 7,036,245 B2 | 5/2006 | Russell | |
| 7,168,186 B2 | 1/2007 | Russell | |
| 7,337,559 B2 | 3/2008 | Russell | |
| 7,524,490 B2 | 4/2009 | Geng | |
| 7,805,849 B1 | 10/2010 | Baker, Jr. | |
| 7,824,436 B2 | 11/2010 | Barbut et al. | |
| 7,837,722 B2 | 11/2010 | Barbut et al. | |
| 7,848,799 B2 | 12/2010 | Herndon | |
| 7,877,900 B2 | 2/2011 | Russell | |
| 7,921,580 B2 | 4/2011 | Russell | |
| 7,950,971 B2 | 5/2011 | Hobet et al. | |
| 8,075,605 B2 | 12/2011 | Barbut et al. | |
| 8,241,229 B2 | 8/2012 | Herndon | |
| 8,290,577 B2 | 10/2012 | Brooks et al. | |
| 8,301,232 B2 | 10/2012 | Albert et al. | |
| 8,313,520 B2 | 11/2012 | Barbut et al. | |
| 8,396,541 B2 * | 3/2013 | Zhang | A61B 5/349 600/518 |
| 8,428,683 B2 | 4/2013 | Yoo et al. | |
| 8,430,805 B2 | 4/2013 | Burnett et al. | |
| 8,435,166 B2 | 5/2013 | Burnett et al. | |
| 8,441,356 B1 | 5/2013 | Tedesco et al. | |
| 8,480,723 B2 | 7/2013 | Barbut et al. | |
| 8,494,507 B1 | 7/2013 | Tedesco et al. | |
| 8,509,882 B2 | 8/2013 | Albert et al. | |
| 8,571,622 B2 | 10/2013 | Huiku et al. | |
| 8,611,980 B2 | 12/2013 | Choe et al. | |
| 8,630,633 B1 | 1/2014 | Tedesco et al. | |
| 8,636,748 B2 | 1/2014 | Herndon | |
| 8,669,864 B1 | 3/2014 | Tedesco et al. | |
| 8,688,189 B2 | 4/2014 | Shennib | |
| 8,700,137 B2 | 4/2014 | Albert | |
| 8,721,699 B2 | 5/2014 | Barbut et al. | |
| 8,738,112 B2 | 5/2014 | Choe et al. | |
| 8,761,858 B1 | 6/2014 | Huttner | |
| 8,802,210 B2 | 8/2014 | Vantomme et al. | |
| 8,805,475 B2 | 8/2014 | Kurpad et al. | |
| 8,948,854 B2 | 2/2015 | Friedman et al. | |
| 8,986,187 B2 | 3/2015 | Perkins et al. | |
| 9,002,477 B2 | 4/2015 | Burnett | |
| 9,005,102 B2 | 4/2015 | Burnett et al. | |
| 9,014,778 B2 | 4/2015 | Datta et al. | |
| 9,022,949 B2 | 5/2015 | Herndon | |
| 9,026,202 B2 | 5/2015 | Albert | |
| 9,040,101 B2 | 5/2015 | Heiman et al. | |
| 9,089,254 B2 | 7/2015 | Govari et al. | |
| 9,173,670 B2 | 11/2015 | Sepulveda et al. | |
| 9,202,360 B1 | 12/2015 | Tedesco et al. | |
| 9,215,075 B1 | 12/2015 | Poltorak | |
| 9,220,430 B2 | 12/2015 | Albert | |
| 9,247,911 B2 | 2/2016 | Galloway et al. | |
| 9,254,092 B2 | 2/2016 | Albert et al. | |
| 9,254,095 B2 | 2/2016 | Galloway et al. | |
| 9,307,921 B2 | 4/2016 | Friedman et al. | |
| 9,339,641 B2 | 5/2016 | Rajguru et al. | |
| 9,351,654 B2 | 5/2016 | Albert | |
| 9,375,179 B2 | 6/2016 | Schultz et al. | |
| 9,387,338 B2 | 7/2016 | Burnett | |
| 9,403,000 B2 | 8/2016 | Lyons et al. | |
| 9,420,956 B2 | 8/2016 | Gopalakrishnan et al. | |
| 9,451,975 B2 | 9/2016 | Sepulveda et al. | |
| 9,463,169 B2 | 10/2016 | Heiman et al. | |
| 9,524,253 B2 | 12/2016 | Kim et al. | |
| 9,572,499 B2 | 2/2017 | Gopalakrishnan et al. | |
| 9,579,062 B2 | 2/2017 | Albert | |
| 9,610,459 B2 | 4/2017 | Burnett et al. | |
| 9,630,004 B2 | 4/2017 | Rajguru et al. | |
| 9,649,042 B2 | 5/2017 | Albert et al. | |
| 9,675,512 B2 | 6/2017 | Kare et al. | |
| 9,681,814 B2 | 6/2017 | Galloway et al. | |
| 9,717,435 B2 | 8/2017 | Walker et al. | |
| 9,737,225 B2 | 8/2017 | Datta et al. | |
| 9,757,584 B2 | 9/2017 | Burnett | |
| 9,775,741 B2 | 10/2017 | Barbut et al. | |
| 9,782,097 B2 | 10/2017 | Choe et al. | |
| 9,804,635 B2 | 10/2017 | Kim et al. | |
| 9,814,423 B2 | 11/2017 | Jain et al. | |
| 9,833,158 B2 | 12/2017 | Albert | |
| 9,839,363 B2 | 12/2017 | Albert | |
| 9,867,990 B2 | 1/2018 | Cinbis et al. | |
| 9,888,337 B1 | 2/2018 | Zalewski et al. | |
| 9,894,471 B1 | 2/2018 | Zalewski et al. | |
| 9,907,478 B2 | 3/2018 | Friedman et al. | |
| 9,911,290 B1 | 3/2018 | Zalewski et al. | |
| 9,942,051 B1 | 4/2018 | Poltorak | |
| 10,038,992 B1 | 7/2018 | Zalewski et al. | |
| 10,049,182 B2 | 8/2018 | Chefles et al. | |
| 10,106,776 B2 | 10/2018 | Birla | |
| 10,111,643 B2 | 10/2018 | Schulhauser et al. | |
| 10,124,172 B2 | 11/2018 | Lyons et al. | |
| 10,140,820 B1 | 11/2018 | Zalewski et al. | |
| 10,142,822 B1 | 11/2018 | Zalewski et al. | |
| 10,159,415 B2 | 12/2018 | Gopalakrishnan et al. | |
| 10,159,421 B2 | 12/2018 | Heneghan | |
| 10,165,355 B2 | 12/2018 | Negi et al. | |
| 10,178,974 B2 | 1/2019 | Vasyltsov et al. | |
| 10,187,773 B1 | 1/2019 | Zalewski et al. | |
| 10,219,714 B2 | 3/2019 | Yang | |
| 10,285,608 B2 | 5/2019 | O'Neill et al. | |
| 10,285,617 B2 | 5/2019 | Toth et al. | |
| 10,305,695 B1 | 5/2019 | Poltorak | |
| D852,965 S | 7/2019 | Bahney et al. | |
| D854,167 S | 7/2019 | Bahney et al. | |
| 10,355,730 B1 | 7/2019 | Zalewski et al. | |
| 10,405,767 B2 | 9/2019 | Walker et al. | |
| 10,413,733 B2 | 9/2019 | Mi et al. | |
| 10,423,193 B2 | 9/2019 | Kim et al. | |
| 10,441,602 B2 | 10/2019 | Heiman et al. | |
| 10,478,084 B2 | 11/2019 | Galloway et al. | |
| 10,478,623 B2 | 11/2019 | Chen | |
| 10,485,980 B2 | 11/2019 | Yeh et al. | |
| 10,510,219 B1 | 12/2019 | Zalewski et al. | |
| 10,531,813 B2 | 1/2020 | O'Neill et al. | |
| 10,537,250 B2 | 1/2020 | Albert | |
| 10,537,403 B2 | 1/2020 | Vora et al. | |
| 10,548,500 B2 | 2/2020 | Lim et al. | |
| 10,561,842 B2 | 2/2020 | Yeh et al. | |
| 10,573,134 B1 | 2/2020 | Zalewski et al. | |
| 10,582,358 B1 | 3/2020 | Zalewski et al. | |
| 10,586,623 B2 | 3/2020 | Avitan | |
| 11,490,849 B2 * | 11/2022 | Kale | A61B 5/1102 |
| 11,576,617 B2 * | 2/2023 | Mortara | A61B 5/7203 |
| 2002/0023374 A1 | 2/2002 | Russell | |
| 2002/0157280 A1 | 10/2002 | Russell | |
| 2003/0032993 A1 | 2/2003 | Mickle et al. | |
| 2003/0199778 A1 | 10/2003 | Mickle | |
| 2003/0212319 A1 | 11/2003 | Magill | |
| 2004/0006891 A1 | 1/2004 | Russell | |
| 2004/0123493 A1 | 7/2004 | Russell | |
| 2004/0134097 A1 | 7/2004 | Russell | |
| 2004/0138584 A1 | 7/2004 | Hogan | |
| 2005/0283998 A1 | 12/2005 | Russell | |
| 2006/0041241 A1 | 2/2006 | Herndon | |
| 2006/0099194 A1 | 5/2006 | Geng | |
| 2006/0156580 A1 | 7/2006 | Russell | |
| 2006/0224072 A1 | 10/2006 | Shennib | |

(56) References Cited

U.S. PATENT DOCUMENTS

| | | |
|---|---|---|
| 2006/0264767 A1 | 11/2006 | Shennib |
| 2006/0276552 A1 | 12/2006 | Barbut et al. |
| 2007/0009542 A1 | 1/2007 | Levin et al. |
| 2007/0123813 A1 | 5/2007 | Barbut et al. |
| 2007/0144037 A1 | 6/2007 | Russell |
| 2007/0149887 A1 | 6/2007 | Hwang et al. |
| 2007/0190651 A1 | 8/2007 | Geng |
| 2008/0004613 A1 | 1/2008 | Barbut et al. |
| 2008/0234594 A1 | 9/2008 | Brooks et al. |
| 2008/0249188 A1 | 10/2008 | Barbut et al. |
| 2008/0263895 A1 | 10/2008 | Russell |
| 2008/0281180 A1 | 11/2008 | Choe et al. |
| 2008/0306325 A1 | 12/2008 | Burnett et al. |
| 2009/0037611 A1 | 2/2009 | Richter |
| 2009/0130623 A1 | 5/2009 | Crohn et al. |
| 2009/0210956 A1 | 8/2009 | Geng |
| 2009/0227829 A1 | 9/2009 | Burnett et al. |
| 2009/0227831 A1 | 9/2009 | Burnett et al. |
| 2009/0234179 A1 | 9/2009 | Burnett et al. |
| 2009/0234325 A1 | 9/2009 | Rozenberg et al. |
| 2009/0318793 A1 | 12/2009 | Datta et al. |
| 2009/0318796 A1 | 12/2009 | Datta et al. |
| 2010/0005685 A1 | 1/2010 | Russell |
| 2010/0036231 A1 | 2/2010 | Hobet et al. |
| 2010/0056871 A1 | 3/2010 | Govari et al. |
| 2010/0115791 A1 | 5/2010 | Russell |
| 2010/0160712 A1 | 6/2010 | Burnett et al. |
| 2010/0168501 A1 | 7/2010 | Burnett et al. |
| 2010/0204538 A1 | 8/2010 | Burnett et al. |
| 2010/0211140 A1 | 8/2010 | Barbut et al. |
| 2010/0222629 A1 | 9/2010 | Burnett et al. |
| 2010/0298687 A1 | 11/2010 | Yoo et al. |
| 2011/0021863 A1 | 1/2011 | Burnett et al. |
| 2011/0028938 A1 | 2/2011 | Barbut et al. |
| 2011/0040237 A1 | 2/2011 | Herndon |
| 2011/0046507 A1 | 2/2011 | Herndon |
| 2011/0046626 A1 | 2/2011 | Herndon |
| 2011/0160601 A1 | 6/2011 | Wang et al. |
| 2011/0265345 A1 | 11/2011 | Russell |
| 2012/0053432 A1 | 3/2012 | Huiku et al. |
| 2012/0083764 A1 | 4/2012 | Barbut et al. |
| 2012/0109258 A1 | 5/2012 | Cinbis et al. |
| 2012/0165644 A1 | 6/2012 | Schultz et al. |
| 2012/0302821 A1 | 11/2012 | Burnett |
| 2013/0053674 A1 | 2/2013 | Volker |
| 2013/0072746 A1 | 3/2013 | Burnett et al. |
| 2013/0096448 A1 | 4/2013 | Brooks et al. |
| 2013/0150698 A1 | 6/2013 | Hsu et al. |
| 2013/0184599 A1 | 7/2013 | Friedman et al. |
| 2013/0231546 A1 | 9/2013 | Choe et al. |
| 2013/0237864 A1 | 9/2013 | Mazar et al. |
| 2014/0046188 A1 | 2/2014 | Yen et al. |
| 2014/0046423 A1 | 2/2014 | Rajguru et al. |
| 2014/0068116 A1 | 3/2014 | Kim et al. |
| 2014/0094808 A1 | 4/2014 | Herndon |
| 2014/0148714 A1 | 5/2014 | Mamaghanian et al. |
| 2014/0148870 A1 | 5/2014 | Burnett |
| 2014/0163304 A1 | 6/2014 | Burnett et al. |
| 2014/0213879 A1 | 7/2014 | Choe et al. |
| 2014/0276262 A1 | 9/2014 | Kare et al. |
| 2014/0303647 A1 | 10/2014 | Sepulveda et al. |
| 2014/0328806 A1 | 11/2014 | Birla |
| 2014/0343641 A1 | 11/2014 | Barbut et al. |
| 2014/0358193 A1 | 12/2014 | Lyons et al. |
| 2015/0073230 A1 | 3/2015 | Stergiou |
| 2015/0094557 A1 | 4/2015 | Hsu et al. |
| 2015/0105640 A1 | 4/2015 | Friedman et al. |
| 2015/0141791 A1 | 5/2015 | O'Neill et al. |
| 2015/0141792 A1 | 5/2015 | O'Neill et al. |
| 2015/0202454 A1 | 7/2015 | Burnett |
| 2015/0234986 A1 | 8/2015 | Dantsker et al. |
| 2015/0335288 A1 | 11/2015 | Toth et al. |
| 2015/0351690 A1 | 12/2015 | Toth et al. |
| 2015/0351799 A1 | 12/2015 | Sepulveda et al. |
| 2015/0359964 A1 | 12/2015 | Walker et al. |
| 2016/0029906 A1 | 2/2016 | Tompkins et al. |
| 2016/0067515 A1 | 3/2016 | Burnett et al. |
| 2016/0067517 A1 | 3/2016 | Burnett |
| 2016/0074671 A1 | 3/2016 | Burnett et al. |
| 2016/0183829 A1 | 6/2016 | Friedman et al. |
| 2016/0193466 A1 | 7/2016 | Burnett |
| 2016/0206876 A1 | 7/2016 | Rajguru et al. |
| 2016/0246940 A1 | 8/2016 | Jain et al. |
| 2016/0249817 A1 | 9/2016 | Mazar et al. |
| 2016/0262691 A1 | 9/2016 | Jain et al. |
| 2016/0287122 A1 | 10/2016 | Heneghan |
| 2016/0302725 A1 | 10/2016 | Schultz et al. |
| 2016/0331974 A1 | 11/2016 | Lyons et al. |
| 2016/0359150 A1 | 12/2016 | de Francisco Martin et al. |
| 2017/0034618 A1 | 2/2017 | Negi et al. |
| 2017/0055900 A1 | 3/2017 | Jain et al. |
| 2017/0135595 A1 | 5/2017 | Baek et al. |
| 2017/0215752 A1 | 8/2017 | Chen |
| 2017/0215754 A1 | 8/2017 | Brooks et al. |
| 2017/0225005 A1 | 8/2017 | Burnett et al. |
| 2017/0231520 A1 | 8/2017 | Yang |
| 2017/0265838 A1 | 9/2017 | Schulhauser et al. |
| 2017/0266443 A1 | 9/2017 | Rajguru et al. |
| 2017/0333712 A1 | 11/2017 | Chen |
| 2017/0340233 A1 | 11/2017 | Kuster |
| 2017/0344736 A1 | 11/2017 | Lane |
| 2017/0354831 A1 | 12/2017 | Burnett |
| 2018/0050216 A9 | 2/2018 | Burnett |
| 2018/0055373 A1 | 3/2018 | Kraiter et al. |
| 2018/0085593 A1 | 3/2018 | Fayram et al. |
| 2018/0146875 A1 | 5/2018 | Friedman et al. |
| 2018/0199842 A1 | 7/2018 | Walker et al. |
| 2018/0247029 A1 | 8/2018 | Fish et al. |
| 2018/0279879 A1 | 10/2018 | Both |
| 2018/0316781 A1 | 11/2018 | Salem |
| 2018/0317797 A1 | 11/2018 | Manera |
| 2018/0368495 A1 | 12/2018 | Simmons |
| 2019/0008396 A1 | 1/2019 | Baron |
| 2019/0040360 A1 | 2/2019 | Birla |
| 2019/0147721 A1 | 5/2019 | Avitan et al. |
| 2019/0151604 A1 | 5/2019 | Harper et al. |
| 2019/0182357 A1 | 6/2019 | Salem |
| 2019/0213862 A1 | 7/2019 | Avitan |
| 2019/0214153 A1 | 7/2019 | Avitan |
| 2019/0223749 A1 | 7/2019 | Toth et al. |
| 2019/0239724 A1 | 8/2019 | Averbuch et al. |
| 2019/0246966 A1 | 8/2019 | Friedman et al. |
| 2019/0254523 A1 | 8/2019 | Avitan |
| 2019/0259268 A1 | 8/2019 | Avitan |
| 2019/0261153 A1 | 8/2019 | Avitan |
| 2019/0261912 A1 | 8/2019 | Shepherd et al. |
| 2019/0290137 A1 | 9/2019 | Zhang et al. |
| 2019/0320974 A1 | 10/2019 | Alzamzmi et al. |
| 2019/0336038 A1 | 11/2019 | Gorgutsa et al. |
| 2019/0341954 A1 | 11/2019 | Zalewski et al. |
| 2019/0350457 A1 | 11/2019 | Avitan |
| 2019/0363746 A1 | 11/2019 | Zalewski et al. |
| 2019/0366045 A1 | 12/2019 | Filipon et al. |
| 2019/0387989 A1 | 12/2019 | Walker et al. |
| 2020/0000355 A1 | 1/2020 | Khair |
| 2020/0000441 A1 | 1/2020 | Lafon et al. |
| 2020/0107775 A1 | 4/2020 | de Chazal et al. |
| 2020/0118400 A1 | 4/2020 | Zalewski et al. |
| 2020/0118401 A1 | 4/2020 | Zalewski et al. |
| 2020/0121249 A1 | 4/2020 | Talgorn et al. |
| 2020/0126370 A1 | 4/2020 | Zalewski et al. |
| 2020/0139120 A1 | 5/2020 | Rajguru et al. |
| 2020/0160670 A1 | 5/2020 | Zalewski et al. |
| 2020/0161001 A1 | 5/2020 | Toong et al. |
| 2021/0235999 A1* | 8/2021 | Nagasawa ............. A61B 5/363 |

* cited by examiner

LOW-POWER WEARABLE SMART ECG PATCH WITH ON-BOARD ANALYTICS

CROSS REFERENCE TO RELATED APPLICATIONS

The present application is a Non-provisional of, and claims benefit of priority under 35 U.S.C. § 119(e) from, U.S. Provisional Patent Application No. 63/032,506, filed May 29, 2020, the entirety of which is expressly incorporated herein by reference.

FIELD OF THE INVENTION

The present invention relates to the field of distributed processing sensor systems, and more particularly to a micropower ECG telemetry system.

INCORPORATION BY REFERENCE

Citation or identification of any reference herein, or any section of this application shall not be construed as an admission that such reference is available as prior art. The disclosure of each publication and patent listed or referenced herein are hereby incorporated by reference in their entirety in this application, and shall be treated as if the entirety thereof forms a part of this application. Such references are provided for their disclosure of technologies as may be required to enable practice of the present invention, to provide written description for claim language, to make clear applicant's possession of the invention with respect to the various aggregates, combinations, permutations, and subcombinations of the respective disclosures or portions thereof (within a particular reference or across multiple references) in conjunction with the combinations, permutations, and subcombinations of various disclosure provided herein, to demonstrate the technological non-abstract nature of the inventions claimed, and for any other purpose. Except as expressly indicated, the scope of the invention is inclusive, and therefore the disclosure of a technology or teaching within these incorporated materials is intended to encompass that technology or teaching as being an option of, or an addition to, other disclosure of the present invention. Likewise, the combination of incorporated teachings consistent with this disclosure is also encompassed. The citation of references is intended to be part of the disclosure of the invention, and not merely supplementary background information. While cited references may be prior art, the combinations thereof and with the material disclosed herein is not admitted as being prior art.

The incorporation by reference does not extend to teachings which are inconsistent with the invention as expressly described herein as being essential. The incorporated references are rebuttable evidence of a proper interpretation of terms, phrases, and concepts employed herein by persons of ordinary skill in the art. No admission is made that any incorporated reference is analogous art to the issues presented to the inventor, and the selection, combination, and disclosure of these disparate teachings is itself a part of the invention herein disclosed.

BACKGROUND OF THE INVENTION

Recent advances in wearable technology have enabled the realization of a variety of smart sensors for health monitoring aimed at individual users. Extensive studies [24,26,34, 36] have discussed the challenges in wearable system for healthcare applications. These studies show that long battery life is imperative for the end-user and a comfortable wearable solution is necessary. Furthermore, it desirable to have a wearable sensor that can be easily worn under apparel. Such sensors can collect important data like ECG, respiratory rate and calculate human performance/clinical parameters such as Heart Rate (HR), Heart Rate Variability (HRV), and more. The acquired data can be used for performance and wellness monitoring, including the reporting of clinically meaningful variations of key sensed data for healthy subjects and subjects at risk, elderly subjects and subjects engaged in potentially stressful activities. Some desirable attributes of these wearable sensors are: (a) power consumption needs to be grossly limited, as they are battery powered; (b) the data acquisition process should be both accurate and reliable; (c) the device should be as unobtrusive as possible for comfort and cosmetics, and (d) the privacy of the acquired data must be ensured, as the acquired data is monitored remotely.

In recent years, wearable ECG or heart rate sensors have entered the market in various forms and have also been developed in the research community. Generally, they appear to have a variety of limitations compared to SEP. ECG sensors, such as Biostamp [15] are incapable of acquiring and sending ECG data continuously—they need to be taken off the subject for transferring the acquired data stored on-board to a host for eventual processing. CALM-M [2] requires external interrogation to transmit data to a host for interpretation. The sensors of [13] and [18] can send ECG signals continuously but lack aggressive power management and on-board analytics thereby limiting their usefulness in longer-term monitoring situations. The device described in [22] limits transmission power based on received signal strength (as SEP does), but other forms of power management are lacking.

Devices such as Apple watch series 4 and Amazfit Health band, both compared in [20], require the wearer's intervention to transmit ECG signals—a consequence of the limitations of on-board electronics to save power. Other ECG-only-on-demand sensors include AliveCor Kardiaband, Omron Complete and WIWE—all described in [20]. Many ECG sensors are either bulky [7, 9] or require belts or belt-like harnesses carrying the sensors to be worn, such as Qardiocore [20], Eco-ECG [12], HeartBit [20] and the sensor of [18], while others require wrist straps on both hands [9].

On-board analytics on a wearable ECG sensor is critical for monitoring the subject's condition. All existing sensors lack this capability and require analysis on an off-board device (such as cell phones, for most of the sensors described earlier) or the Cloud [1, 4].

Some cloud-based solutions, such as [29], do not really have long battery life and any aggressive power monitoring implementations. Other devices [30,31,32,33,35,38,39] have most, or all, rely on off-board analysis of the acquired ECG signals on a PC or a mobile system. Often the processing is not done as the signal in real-time, making these devices unusable for critical, live monitoring situations. Also, these devices do not have any artifact detection induced by motion, or aggressive noise cancelling techniques.

SUMMARY OF THE INVENTION

The present technology provides a self-contained wearable smart ECG wearable device, e.g., a Smart ECG Patch (SEP) in the form of a flexible patch with embedded gold electrodes, and onboard electronics for acquiring ECG signals, digitizing the ECG signal and processing the digitized signal for detecting inevitable noise/motion artifacts and deriving the heart rate and heart rate variability parameters. The patch may communicate the ECG signal and the computed heart rate/heart rate variability values to a host via a secure Bluetooth link. The onboard electronics may also be capable of generating alert signals when the heart rate and heart rate variability cross user-specific pre-specified thresholds; other alarm thresholds can also be set. The patch can be configured remotely to operate in a variety of power savings mode where data is transmitted only under the configured alarm conditions. Further, the SEP can be placed on the lower left ribcage of the subject, away from the subject's heart and hidden under normal clothing—a feature that makes it attractive to those who are reluctant to wear similar monitors because the sensors are visible to others. The SEP may be adhered to the subject's body by using a double-sided adhesive tape with large cutouts for the electrode areas. The cutout areas may enclose and contain a medical contact gel. FIG. 2A shows the SEP with some of its main components highlighted. FIG. 2B shows a representative cross section of a flexible circuit substrate. A Kapton substrate 12 is metallized with a copper layer 13, with printed sensors 16, e.g., electrodes. A solder mask 14 protects the exposed metal and sensor material, with gaps defining a well for contact gel 15, and for surface mounting of a component 11 on solder bumps 17. Advantageously, an antenna 18 for radio frequency communication may be formed as a metallized region or regions on the Kapton substrate 12.

The technology was implemented in a prototype, that uses discrete electronics component in packages. The design can be implemented as a 2 inch square patch, shown in FIG. 2A. With the use of bare dies on a flexible substrate, the sensor can be realized as a 1.25 inch by 2-inch (or smaller) patch. As shown in FIG. 2A, the microprocessor, memory, and Bluetooth functions may be provided on a modular circuit 2, which is then placed on the flexible substrate 1. Alternately, the microprocessor and/or transceiver may be mounted directly on the substrate, if appropriate electromagnetic interference suppression and especially in the case of the antenna 3, impedance control is achieved. The flexible substrate has two electrodes 4, 5 formed on the rear side, which produce signals processed by an analog front end circuit 6. An analog filter circuit 7 is provided implemented as additional components provided on the substrate. A coin cell lithium battery 8 powers the system.

The SEP differs from ECG sensors developed in the research community that lack onboard R-peak detection capabilities [41-49]. An example of such sensors is the passive ECG signal acquisition device on a belt with widely separated electrodes and designed to operate continuously that lacks power management features, on-board active signal processing for reducing motion artifacts and for estimating HR/HRV [41]. Another example is described in [50]. Many sensors also rely on off-board processing for deriving the HR and HRV values, and use more than two electrodes [43-45, 48, 49]. SEP also differs from existing research prototypes or products that are not designed for continuous operation or require hand pressure, additional support or belts to engage the electrode reliably with the subject, nor requires acquisition to be interrupted to permit the sensor to be relocated for downloading the acquired ECG signal [17, 20]. ECG-Watch [51] is a wristwatch-like device for acquiring and sending signals to a host device on interrogation for further analytics and incorporates embedded analytics algorithm for detecting atrial fibrillation (AFib). SEP as implemented in the prototype, lacks the onboard AFib detection capability of ECG watch but has about one-third of the power requirements of ECG-Watch for transmission as well as acquisition, and can run for much longer durations, perform other on-board signal analytics, trigger transmissions on its own on sensing abnormal conditions and can be worn discreetly under the clothing. Of course, and atrial fibrillation-detection algorithm may be implemented in SEP, with consequent increase in processing power. SEP measures 2 inches square and is shown in FIG. 2A. Some other remote monitoring ECG systems [23, 32, 33] used for tele-medicine and home care solutions do not specify aggressive power management techniques and implement most of the signal post processing offboard on a wireless host like a PC.

An earlier version of the sensor that was only capable of ECG signal acquisition was described in [13] where processing was done offboard on a Bluetooth host, and had no incorporation of any power management technique. In contrast, the present technology provides an enhanced system, specifically, onboard software algorithms used to detect R-peaks in QRS complex of an ECG signal, for detecting noise/motion artifacts, and reducing overall power consumption very aggressively.

On-board signal acquisition with automatic artifact removal and its analysis on-board (heart rate, heart rate variability generation) permit generation of alarms during monitoring and for conserving power to prolong battery life. This is precisely where SEP appears to have a significant advantage over other sensors described above, in addition to being easily wearable.

A battery-operated wearable device capable of acquiring electrocardiogram (ECG) signals and data for the wearer is therefore provided. The device performs local signal processing to remove noise and signal artifacts, to generate additional clinical data of interest and to generate alarm signals based on pre-specified parameter thresholds. The device may also detect sudden movements by the wearer.

All acquired data, parameters and alarms generated on the device can be sent to a host device using a secure wireless link, e.g., BLE or Zigbee. The device is also capable of operating in a number of modes to conserve battery power and to prolong its operation time without recharging or replacing the battery on the device.

A microcontroller within the patch device controls the acquisition of the ECG signal from the wearer, performs preprocessing to reduce signal noise and motion artifacts to recover a usable ECG signal and control the overall mode of operations of the sensor, including power management, communication with a host device and generation of alarms.

The device addresses an important need to have a small and easily wearable, wire-free ECG sensor that operates for a long time on a single small non-rechargeable battery (or on a charged small rechargeable battery) and is capable of generating ECG data, parameters of interest and alarms.

The data, once transmitted may be further processed or displayed on a Bluetooth host (or other host device), or further relayed to a server, cloud, or destination for processing, analysis, storage/archive, and user interface.

In one implementation, the ECG patch may relay ECG signals of interest to a processing center, a physician, and/or an emergency medical services provider. The destination may be preprogrammed, determined within the ECG patch, determined by the host device, or determined by a remote server.

The device is self-contained as a wire-free device and in its inclusion of local signal processing for noise and artifact removal, for detecting sudden movements of the wearer that indicate potential emergencies like a fall or collapse of the wearer and generating alarms based on sensed cardiac conditions and movement while supporting a number of power-saving operating modes and transitions in-between such operating modes based on sensed data.

It is therefore an object to provide an electrocardiogram sensor, comprising: an analog processing component configured to process a signal comprising cardiac electrical activity; a digitizer configured to create a digital representation of the signal; a microprocessor, configured to: receive the digital representation of the signal; process the digital representation to determine at least one electrocardiographic feature and periods the digital representation of the signal represents artifact; analyze the determined at least one electrocardiographic feature to determine at least heart rate; contingently generate information packets having a plurality of different information types, the information packets having a respective information type dependent on at least the determined at least one electrocardiographic feature and the determined periods representing artifact; and a wireless communication device, under control of the microprocessor, configured to remain in a non-transmitting low power state without transmitting information packets for the periods representing artifact, and to enter a transmitting high power state for transmission of the contingently generated information packets containing valid statistics for at least the heart rate, and subsequently revert to the low power state after transmission.

It is also an object to provide a method for operating an electrocardiogram sensor, comprising: processing a signal comprising cardiac electrical activity received from a set of electrodes with an analog processing component; digitizing the processed signal to create a digital representation of the signal; automatically processing the digital representation to determine at least one electrocardiographic feature and periods the digital representation of the signal represents artifact during which cardiac electrical activity is unavailable; analyzing the at least one determined electrocardiographic feature to determine at least heart rate; contingently generating information packets having a plurality of different information types, the information packets having a respective information type dependent on at least the determined at least one electrocardiographic feature and the determined periods representing artifact; and wirelessly communicating the information packets, under control of a microprocessor, to remain in a non-transmitting low power state without transmitting information packets for the periods representing artifact, and to enter a transmitting high power state for transmission of the contingently generated information packets containing valid statistics for at least the heart rate, and subsequently revert to the low power state after transmission.

The wirelessly communicating may comprise transmitting a radio frequency signal through an antenna formed on a flexible substrate supporting the microprocessor and at least two of the set of electrodes configured to acquire an electrocardiographic signal through human skin; further comprising: receiving a command through the antenna to control the microprocessor; buffering electrocardiographic data with the microprocessor in a memory, periodically forming an information packet from the buffered electrocardiographic data; and overwriting the buffered electrocardiographic data after transmission. The wireless communication may be radio frequency (Bluetooth/BLE, WiFi, 3G, 4G, 5G, 6G), and may alternately be light (e.g., infrared, visible light, ultraviolet), acoustic (ultrasonic, audible), backscatter optical or radio frequency communications (e.g., RFID standards EPC UHF Gen2v2 or ISO/IEC 18000, ISO 14443, ISO 15693, NFC), or the like.

The method may further comprise extracting a plurality of electrocardiographic features from the cardiac electrical activity; and transmitting at least one of the plurality of electrocardiographic features and a series of samples from the digitizer in the contingently generated information packets selectively in dependence on said automatic processing.

The method may further comprise determining an electrocardiographic alarm state based on said automatic processing selectively during periods without artifact, and communicating an alert selectively in dependence on the determined electrocardiographic alarm state.

It is a further object to provide a non-transitory computer readable medium for controlling at least one microprocessor operating an electrocardiogram sensor, comprising: instructions for digitizing a signal from a set of electrodes to create a digital representation of the signal; instructions for processing the digital representation to determine at least one electrocardiographic feature and periods the digital representation of the signal represents artifact; instructions for analyzing the at least one determined electrocardiographic feature to determine at least heart rate; instructions for contingently generating information packets having a plurality of different information types, the information packets having a respective information type dependent on at least the determined at least one electrocardiographic feature and the determined periods representing artifact; and instructions for communicating the information packets, to remain in a non-transmitting state without transmitting information packets for the periods representing artifact, and to enter a transmitting state for transmission of the contingently generated information packets containing valid statistics for at least the heart rate, and subsequently revert to the non-transmitting state after transmission.

A substrate may be provided for supporting the microprocessor, a set of electrodes for receiving the signal comprising cardiac electrical activity, and a self-contained power source, configured to power the analog processing component, e.g., an amplifier, the digitizer, the microprocessor, and the wireless communication device. The substrate may be a flexible substrate having at least two of the set of electrodes formed on the flexible substrate, configured to receive the transdermal bioelectric signals representing the cardiac electrical activity through human skin; and an adhesive layer configured to adhere with flexible substrate to human skin, without interference with the set electrodes.

The microprocessor may be further configured to determine heart rate variability, and the contingently generated information packets further contain valid statistics for at least the heart rate variability. The microprocessor may be configured to: maintain a data buffer for electrocardiographic data in a memory, periodically form an information packet from the maintained electrocardiographic data; and overwrite the contents of the data buffer with subsequent electrocardiographic data. The microprocessor may be configured to extract a plurality of electrocardiographic features from the cardiac electrical activity, and transmit at least one of the plurality of electrocardiographic features and a series of samples from the digitizer representing the cardiac electrical activity in the contingently generated information packets. The microprocessor may be further configured to determine an electrocardiographic alarm state, and to transmit an alert selectively dependent on the determined electrocardiographic alarm state. The microprocessor may be further configured to receive control information through the wireless communication device which determines an energy consumption rate of the electrocardiogram sensor patch.

The microprocessor may be configured to analyze the determined at least one electrocardiographic feature to determine at least heart rate by determining occurrence of R waves.

The microprocessor may be further configured to automatically: process the digital representation to determine a baseline representing a statistical reference signal level; store the data representing the baseline in a memory; determine a leads-off condition of an electrocardiographic electrode; and redetermine the baseline after the leads off condition has abated.

The microprocessor may be further configured to automatically process the digital representation with respect to the baseline, to detect an artifact.

The microprocessor may be further configured to determine occurrence of a cardiac arrhythmia, and to selectively contingently generate the information packets comprising information indicative of the cardiac arrythmia.

The microprocessor may be further configured to automatically process the digital representation to determine valid cardiac statistics.

The microprocessor may be further configured to control the wireless communication device to communicate the digital representation subsequent to the determined occurrence of the cardiac arrhythmia, and to control the wireless communication device to communicate a set of parameters characterizing the cardiac electrical activity but not comprising the digital representation prior to the determined occurrence of the cardiac arrhythmia.

A microprocessor-implemented biological model of expected cardiac electrical activity may be maintained in the SEP, and wherein the periods representing artifact represent periods during which the digital representation of the electrocardiographic signal includes unexpected values with respect to the microprocessor implemented biological model.

The substrate may comprise a flexible substrate having at least two electrodes adapted for skin contact, configured to receive the transdermal bioelectric signals representing the cardiac electrical activity, further comprising an adhesive layer configured to adhere with flexible substrate to human skin, without interference with the at least two electrodes making skin contact.

The periods representing artifact may comprise periods of at least one of noise artifacts, motion artifacts, and electrode non-contact artifacts.

It is also an object to provide a method for operating a wearable electrocardiogram sensor patch, comprising: providing a patch having an amplifier configured to amplify an electrocardiographic signal representing cardiac electrical activity, a digitizer configured to create a digital representation of the electrocardiographic signal, a microprocessor, a radio frequency transceiver having an antenna, and a self-contained power source, configured to power the amplifier, the digitizer, the microprocessor, and the radio frequency transceiver; receiving the digital representation of the electrocardiographic signal; determining periods of artifact; processing the digital representation to determine electrocardiographic features; analyzing the determined electrocardiographic features to determine at least heart rate; adaptively generating information packets having a plurality of different information types, the information packets having a respective information type dependent on at least the determined electrocardiographic features and the determined periods of artifact; and transmitting the adaptively generated information packets containing valid statistics for at least the heart rate, and remaining in a non-transmitting low power state without transmitting information packets for the determined periods of artifact.

It is also an object to provide a non-transitory computer readable medium for controlling at least one microprocessor operating a wearable electrocardiogram sensor patch, comprising: instructions for receiving a digital representation of the electrocardiographic signal from a digitizer; instructions for processing the digital representation to determine a baseline; instructions for determining a need to redetermine the baseline based on artifacts within the digital representation of the electrocardiographic signal; instructions for processing the digital representation to determine electrocardiographic features; instructions for analyzing the determined electrocardiographic features to determine at least heart rate; instructions for adaptively generating information packets having a plurality of different information types, the information packets having a respective information type dependent on at least the determined electrocardiographic features and a deviance of the digital representation of the electrocardiographic signal from the baseline; and instructions for controlling a transceiver to transmit the adaptively generated information packets containing valid statistics for at least the heart rate, and remaining in a non-transmitting low power state without transmitting information packets for periods of artifact.

It is a further object to provide a non-transitory computer readable medium for controlling at least one microprocessor operating a wearable electrocardiogram sensor patch, comprising: instructions for receiving a digital representation of the electrocardiographic signal from a digitizer; instructions for processing the digital representation to determine digital representations representing artifact; instructions for processing the digital representation to determine electrocardiographic features; instructions for analyzing the determined electrocardiographic features to determine at least heart rate; instructions for adaptively generating information packets having a plurality of different information types, the information packets having a respective information type dependent on at least the determined electrocardiographic features and the determined digital representations representing artifact; and instructions for controlling a transceiver to transmit the adaptively generated information packets containing valid statistics for at least the heart rate, and remaining in a non-transmitting low power state without transmitting information packets having information corrupted by the determine digital representations representing artifact.

A further object provides a wearable electrocardiogram sensor patch, having a substrate comprising: an amplifier configured to amplify an electrocardiographic signal representing cardiac electrical activity; a digitizer configured to create a digital representation of the electrocardiographic signal; a microprocessor, configured to: receive the digital representation of the electrocardiographic signal, determine periods of artifact, process the digital representation to determine electrocardiographic features, analyze the determined electrocardiographic features to determine at least heart rate, and adaptively generate information packets having a plurality of different information types, the information packets having a respective information type dependent on at least the determined electrocardiographic features and the determined periods of artifact; a radio frequency transceiver having an antenna, under control of the microprocessor, configured to transmit the adaptively generated information packets containing valid statistics for at least the heart rate, and to remain in a non-transmitting low power state without transmitting information packets for the determined periods of artifact; and a self-contained power source, configured to power the amplifier, the digitizer, the microprocessor, and the radio frequency transceiver.

The wearable electrocardiogram sensor patch may be configured as a self-contained wearable smart ECG wearable device.

The substrate may be a flexible substrate having at least two electrodes formed on the flexible substrate, configured to receive the transdermal bioelectric signals representing the cardiac electrical activity. The at least two electrodes may comprise a gold surface. The substrate may comprise a flexible substrate having at least two electrodes adapted for skin contact, configured to receive the transdermal bioelectric signals representing the cardiac electrical activity, further comprising an adhesive layer configured to adhere with flexible substrate to human skin, without interference with the at least two electrodes making skin contact. The substrate may comprise a flexible substrate configured to support packed integrated circuits and/or bare die integrated circuits. A printed antenna may be provided on the flexible substrate.

The transceiver may be compliant with IEEE-802.15, or be a Bluetooth transceiver, an ANT transceiver, or a LoPAN transceiver. The transceiver may be multi-protocol. The transceiver may communicate over an encrypted data communication channel.

The microprocessor may be further configured to determine heart rate variability, and the adaptively generated information packets may further contain valid statistics for at least the heart rate variability. The microprocessor may be configured to maintain a data buffer for maintaining electrocardiographic data in memory, to periodically form an information packet from the maintained electrocardiographic data, and to overwrite the contents of the data buffer with subsequent electrocardiographic data. The microprocessor may be further configured to determine an electrocardiographic alarm state, and toe transmit an alert selectively in dependent on the determined electrocardiographic alarm state. The microprocessor may be further configured to receive control information which determines an energy consumption rate through the transceiver. The microprocessor may be further configured to transmit information related to a state of the self-contained power source through the transceiver.

The microprocessor may be further configured to: process the digital representation to determine a baseline; determine a leads-off condition of an electrocardiographic electrode; and redetermine the baseline after the leads off condition has abated.

The microprocessor may be configured to analyze the determined electrocardiographic features to determine at least heart rate by determining occurrence of R waves.

The microprocessor may be further configured to determine occurrence of a cardiac arrhythmia. The microprocessor may be configured to control the transceiver to generate an alarm upon the determined occurrence of the cardiac arrhythmia The microprocessor may be configured to control the transceiver to generate an alarm signal to a local host upon determined occurrence of the cardiac arrhythmia, and to control the host to transmit a corresponding alarm to a remote server upon receipt of the alarm signal.

The microprocessor may have a plurality of power consumption modes comprising a sleep mode and an awake mode, and wherein the microprocessor is programmed to alternate between sleep mode and awake mode in a duty cycle.

The periods of artifact comprise periods of noise artifacts and/or periods of motion artifacts. These artifacts may, in some cases, be suppressed by analog and/or digital filtering, and if suppressed, the electrocardiographic signal processed to determine features during periods of suppressed artifacts. However, if the artifacts are not reliably suppressed, the microcontroller preferably does not calculate cardiac statistics perturbed by the artifacts. The electrocardiographic signal may be received through at least one electrode, and the periods of artifact comprise periods of electrode non-contact artifacts. The microprocessor may be further configured to filter artifacts, to reduce occurrence of periods of artifact.

The wearable electrocardiogram sensor patch may further comprise an analog filter configured to filter artifacts, to reduce occurrence of periods of artifact.

At least the microprocessor, digitizer, and transceiver (i.e., the digital circuitry) may be integrated within a single integrated circuit.

The wearable electrocardiogram sensor patch may communicate with a remote host configured to communicate with the transceiver, to receive the information packets, and transmit control information to at least alter a power consumption of the transceiver.

The technology may reduce power wastage due to transmission of incorrect human subject's data by preprocessing raw acquired data from the sensor, followed by the suppression of data transmission if the acquired data is not in compliance with what is expected, with the expectation being defined as signal parameters remaining within limits that are prespecified.

The technology may reduce power wastage due to transmission of incorrect human subject data by incorporating algorithms to preprocess the raw acquired data from the sensor followed by the suppression of data transmission if the acquired data is not in compliance with what is expected, with the expectation being defined as signal parameters remaining within limits that are derived from historical measurements during device operation. The failure to meet expectation may be considered an artifact. The expectation may alternately be defined as signal parameters remaining within limits that are derived from clinical data pertaining to the specific subject. The expectations may be generated within the SEP, or communicated to it by the host. The limits may be determined adaptively, and for example, may be responsive to activity level, diurnal variation, past history, variability or other statistical properties of prior readings, etc.

Expected signal characteristics and artifacts (i.e., readings whose value does not accurately reflect the biological process being monitored) may be distinguished by signals being out of range, or by patterns which are either similar to known interference patterns, or dissimilar from biological process patterns, or both. Given the typically limited processing power of the locally-executed algorithm(s), upon initial presentation, the SEP may transmit the possibly artefactual data to the host, wherein the host analyzes the signal, and makes a determination, and thereafter communicates an updated profile or algorithm to the SEP to permit reliable filtering. In most cases, the types of artifacts and interference are established in a predetermined manner, and therefore the algorithm executing in the SEP need not be updated. However, in some cases, new types of interference or artifact may emerge.

The SEP may token certain types of data or messages, and intermittently transmit only small messages indicative of its state. These may take the form of a heartbeat message, which advantageously includes a power source state. For example, in many cases, the ECG pattern may be regular, and only the statistics, e.g., heart rate and heart rate variability are transmitted, e.g., every 5 minutes. However, when an arrhythmia is detected, which may be determined by an aberrant ECG waveform and/or interbeat latency which is of an unexpected value, then the transmission may convert to a real-time ECG stream. In this case, "real-time" means that all of the data after appropriate filtering is transmitted, which may be as intermitted packets through the digital packet radio, if the packet data transmission rate exceeds the data acquisition rate, or a stream of packets that may extend beyond the time of the reading if the packet data transmission rate is lower than the data acquisition rate. In any case, a duration of readings, e.g., 60 seconds or 300 seconds, is recorded and transmitted to the host, and the host may analyze the readings and/or forward them to a remote server or processing center.

The communication between the SEP and host is typically encrypted. In some cases, the SEP may engage in a virtual private network communication with a remote server or center, permitting the local host to be untrusted. See, U.S. Pat. Nos. 10,305,695; 9,942,051; and 9,215,075, and references incorporated therein.

DETAILED DESCRIPTION OF THE PREFERRED EMBODIMENTS

Figure 1:
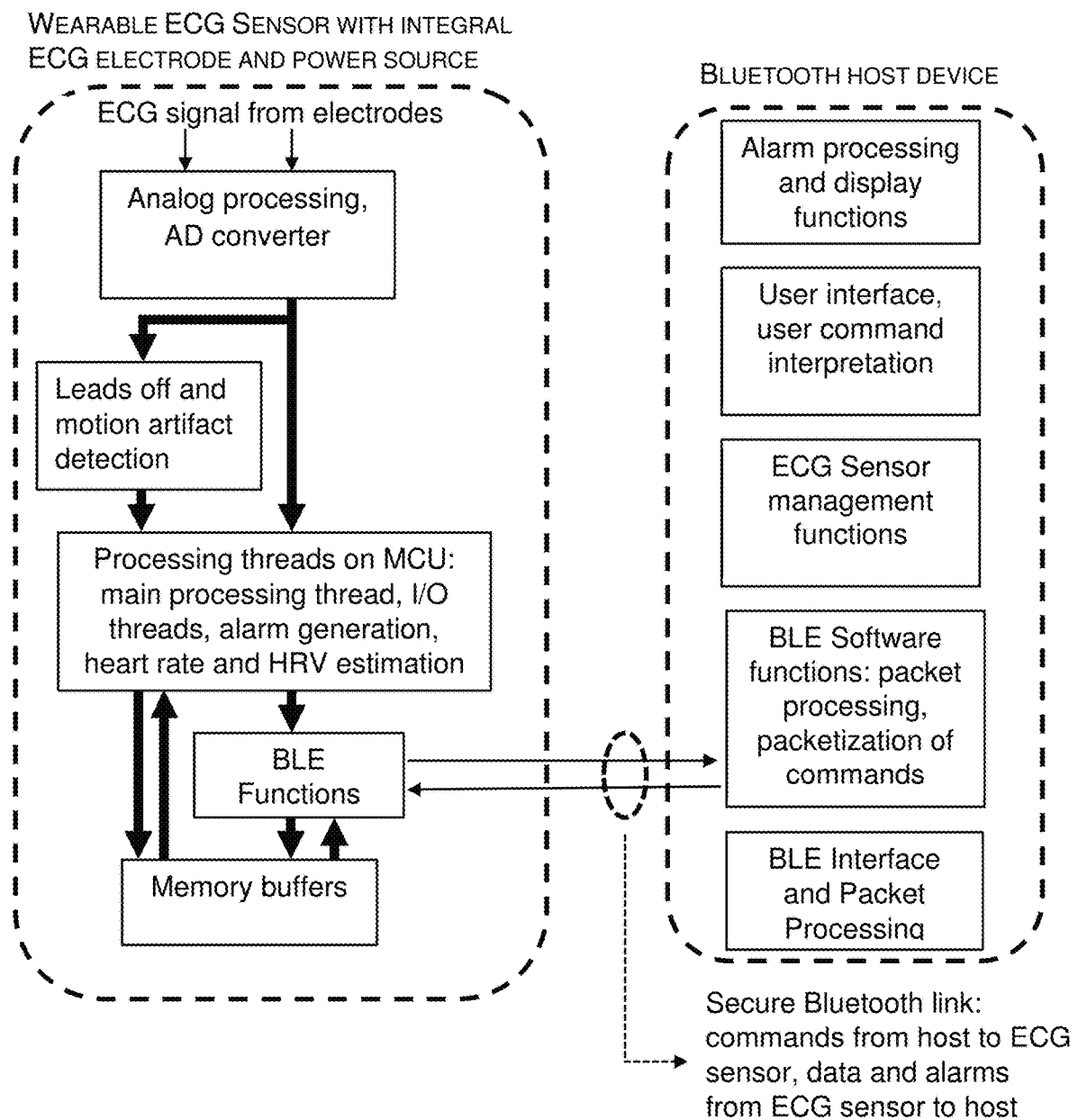
FIG. 1 shows a high level diagram of functions of SEP and a Bluetooth host.
Figure 2A:
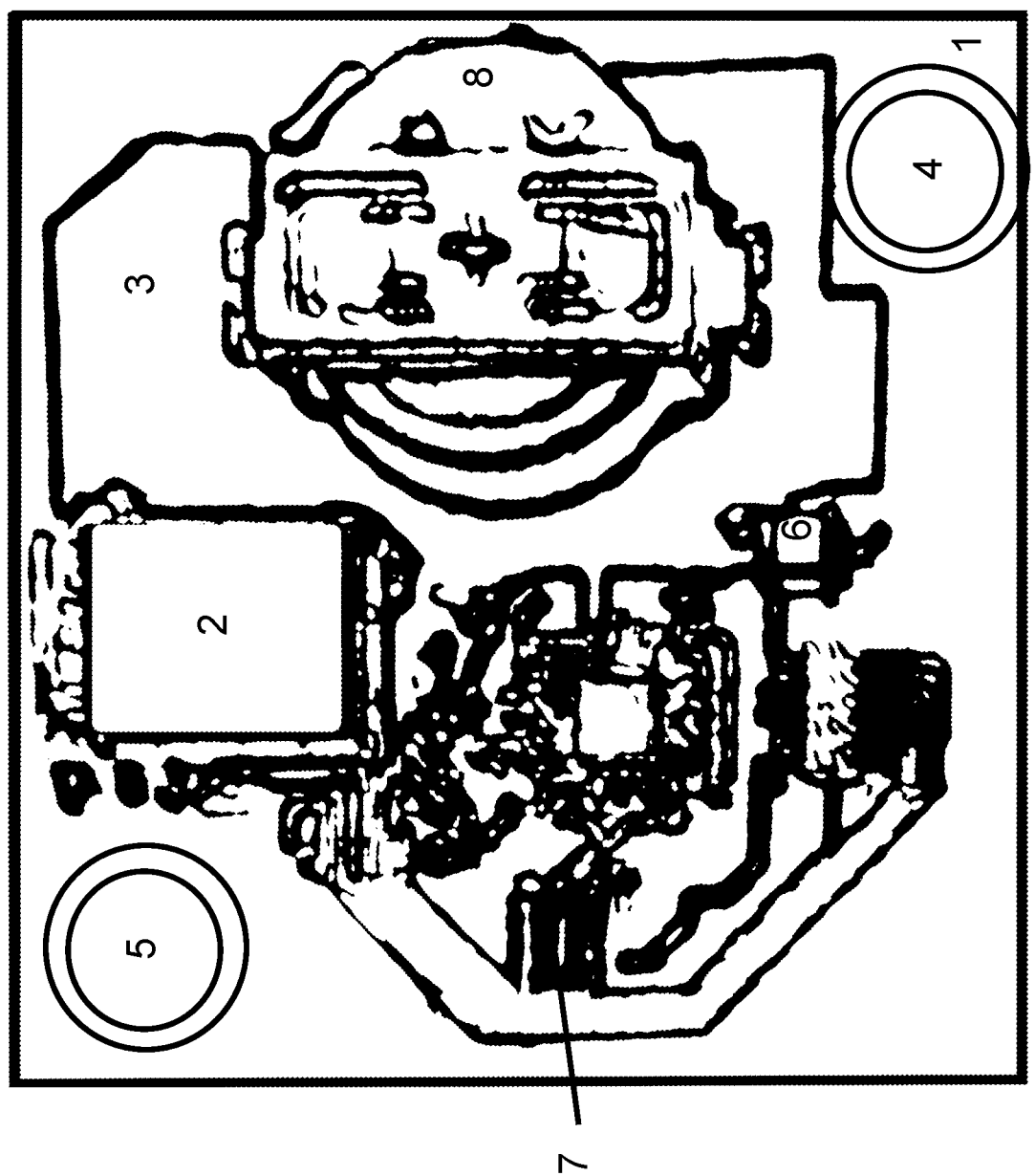
FIG. 2A shows the SEP with locations of ECG electrodes on body side of the patch, marked with circles.
Figure 2B:
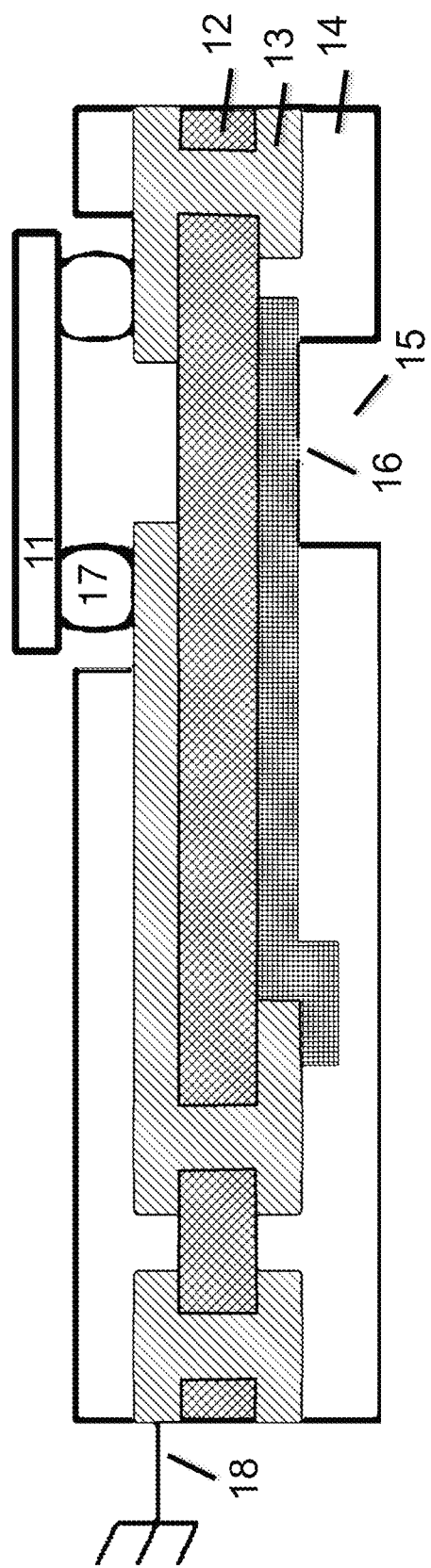
FIG. 2B shows a representative cross section of a flexible circuit substrate.

The overall architecture of the system is shown in FIG. 1. The ECG signal is acquired using a 2-lead configuration where the electrodes are located at the two diagonal ends of the patch on the body side to get the maximum possible spacing between the electrodes and to get the highest possible ECG signal amplitude under the dimensional constraints of the patch. The ECG signal is processed and cleaned up using analog front-end circuitry that filters out signal outside the frequency band of interest using a multi-pole filter. This front-end circuitry also limits current flow into the human subject going through the electrodes in the worst case if circuit damage applies the full battery voltage across the electrodes. The rest of the data acquisition module, Analog to Digital Converter (ADC), signal cleanup, buffering, transmission to a Bluetooth host device is implemented by a micro controller unit (MCU) module. A number of suitable processors are available, including TI CC2640, nRF52832, MSP430, TI CC2530 system CC2431, TMS320VC5509A TMS320F2812, TMDX5505eZDsp/VC5505eZdsp, MSP430F5515, MSP430F1232, MSP430FG439, MSP430F2418 MSP430F5529, MSP430F5419A, ATmega8, ATmega328, PIC18LF4620, and ADuC842. These may be paired with, for example an analog front end (AFE) such as a TI AFE49I30 (ECG with pulse oximeter) or ADS 129X (ECG only). A Real-time Operating System (RTOS) and available libraries provide the main scheduling and support functions. For example, the CC2640 device is a wireless MCU targeting Bluetooth applications. The CC2640 device contains a 32-bit ARM Cortex-M3 processor that runs at 48 MHz as the main processor and a variety of peripherals that include a unique ultralow power sensor controller. This sensor controller interfaces external sensors and for collecting analog and digital data autonomously while the rest of the system is in sleep mode. An ARM Cortex-MO is provided as an RF system controller.

Several software modules perform the functions of the SEP, with each module being executed in a thread. The thread for one process interacts with other thread(s) used in SEP's software via synchronization variables and buffers in the RAM. The Data Acquisition Thread (DAT) controls all aspects of data acquisition, its digitization and the storage of the digitized signal within a buffer within the MCU's RAM. A 12-bit ADC (analog-to-digital converter), operated at a 400 Hz sampling rate, is used. The Main Processing Thread (MPT) examines the digitized data in the buffer, performs R-peak detection and calculates the heart rate and heart rate variability, perform noise and motion artifact removal by signaling the ADT (discussed below) and performs transmission checks as dictated by the operating mode; (iii) An analysis and diagnostics thread (ADT) calculates the HR and HRV and for the MPT; (iv) A transmission thread is responsible for converting the cleaned-up, digitized signals into BLE packets and transmitting it to the host as needed; and (v) A receive thread is responsible for receiving command packets from the Bluetooth host and for interpreting the commands, which are then passed on to the MPT. If data transmission to the host is warranted, the MPT deposits the HR, HRV and/or the digitized ECG signal into the transmission buffer for access by the transmission thread.

The MPT also performs transmission checks as dictated by the power saving modes selected from the host device to prolong battery life. An operating mode can also be changed dynamically, for example, based on alarm signals derived from the ECG waveform by the SEP's noise and motion Artifact Detection Thread (ADT), or based on low battery voltage.

SEP operates in a variety of modes; these modes may be selected from the host device. An operating mode can also be changed dynamically, for example, based on alarm signals derived from the ECG waveform by the sensor's MPT thread or based on the battery voltage or based on commands from the host. SEP's operating modes permit power conservation to increase the operating time. Data sent to the host from SEP can be analyzed further on the cloud for personalized diagnostics, as in the system of [52].

When data transmission to the host is warranted, the MPT deposits the heart rate, heart rate variability and/or the digitized ECG signal into the transmission buffer for access by the transmission thread. The SEP connects to a Bluetooth host using Bluetooth Low Energy (BLE) protocol to transmit the ECG signals, heart rate, heart rate variability, alarms, and other configuration/system data. A Transmit Thread (TT) encapsulates packet payloads in the buffer into BLE packets and transmits it to the host as needed. A Receive Thread (RT) on the SEP receives command packets from the host and interpreting such commands.

Figure 3:
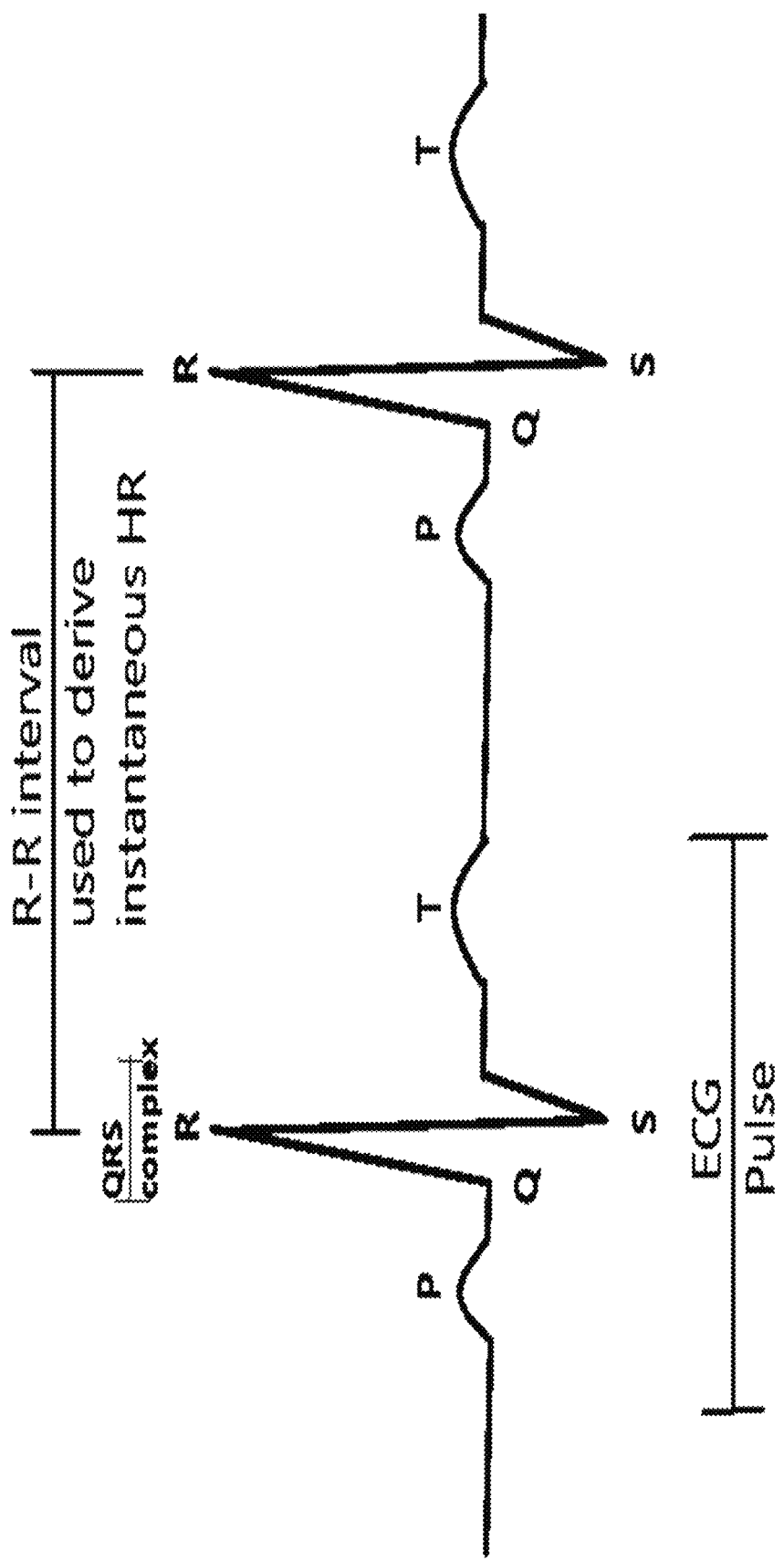
FIG. 3 shows an abstract representation of ECG signal of one period

An ECG signal is a complex signal consisting of three temporally separated waveforms of interest, namely, P, QRS, and T, as shown in an abstract form FIG. 3. The SEP processes real-time ECG signals to calculate the heart rate (HR), and heart rate variability (heart rate variability) parameters by detecting the R-peaks in the QRS complex wave. The period between consecutive R-peaks in the acquired data determines the heart rate, which is the number of R peaks occurring within a period of time, e.g., one minute or one second. The onboard software processes the digitized signal and detects the R-Peaks by sensing the slope changes and the relative amplitude of the signal in relation to other peaks in the ECG waveform.

The R-peak amplitude, as sensed across the electrodes, is typically less than 5 mV. Analog circuitry, e.g., an instrumentation amplifier, amplifies this signal, removes higher frequency components and any 60-Hz pickup from the analog signal using multi-pole filters. The digitized output from the ADC is a 12-bit or 16-bit unsigned integer ranging between 0 and 4095 and is stored in the RAM. A value within this range represents the digitized value of each ECG signal sample.

When first turned on, the thread MPT determines the presence of any input ECG signal using the assistance of the thread ADT before performing any heart rate, or heart rate variability calculation. The MPT determines the baseline reference of the signal in real-time. The initial baseline is the running average of the ECG signal, excluding the R and S peaks. To do this, the SEP is put on the subject and used to acquire a clean signal with the subject at rest. The initial baseline value is calculated from this signal. During this initialization phase, each incoming ECG sample is buffered into the memory for two seconds. Thereafter, the baseline is recalculated continuously to detect motion artifacts by rejecting any high frequency peaks below a specific amplitude range on either side of the current baseline, as described later. The rejected signals are considered as noise.

Figure 4A:
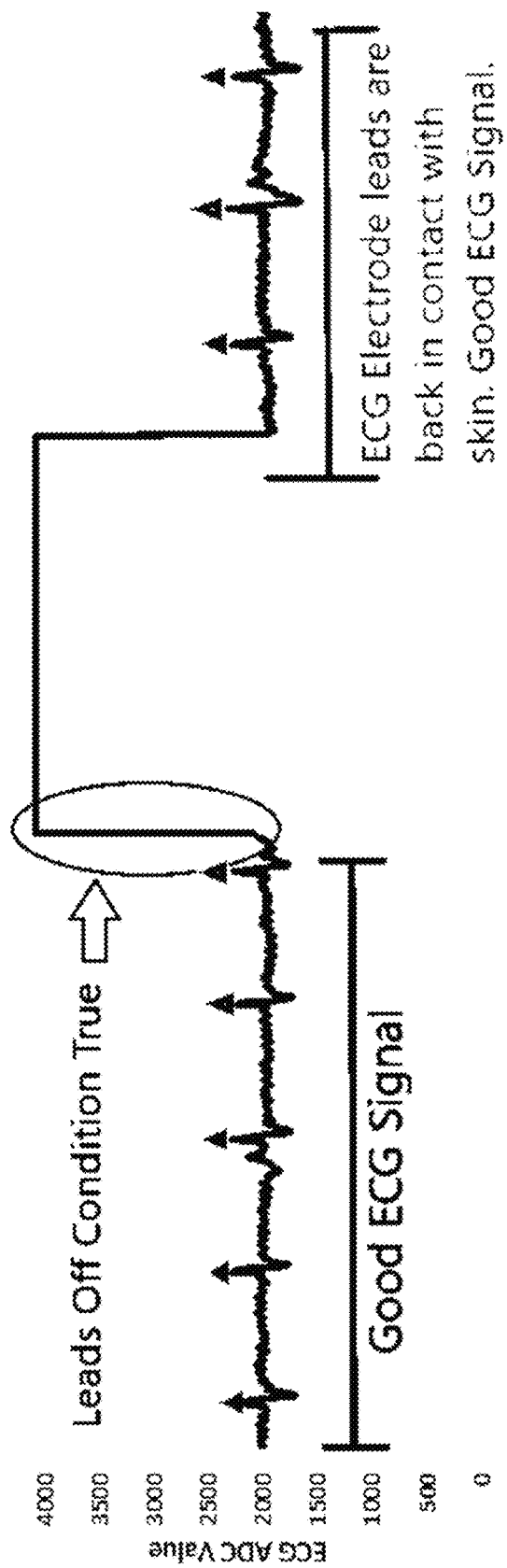
FIG. 4A shows a leads-off detection scenario.
Figure 4B:
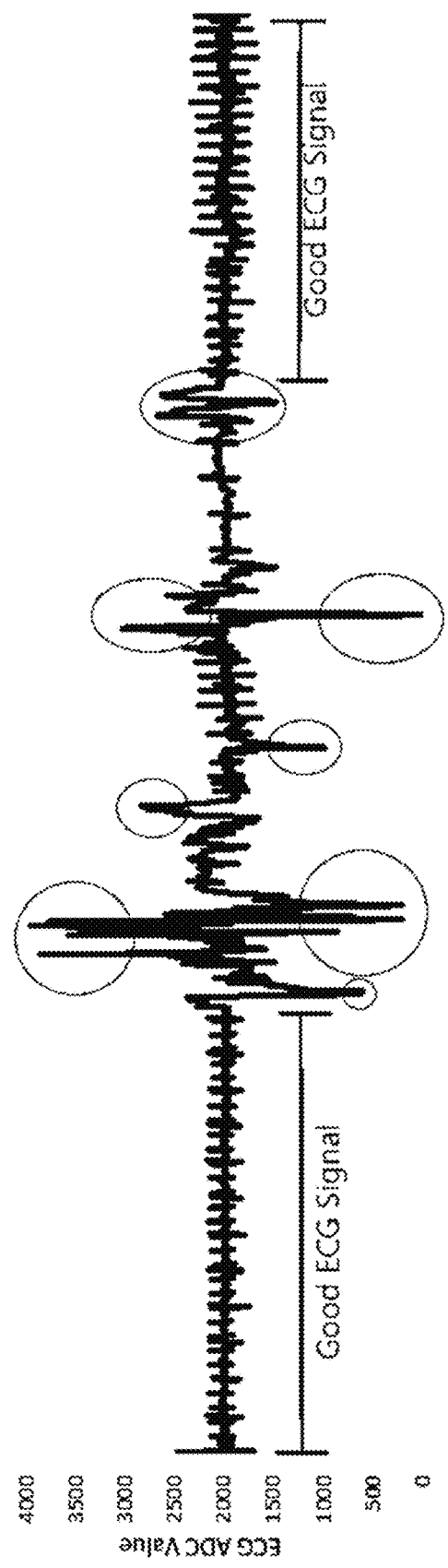
FIG. 4B shows noise/Motion Artifact detection scenario. Circles show the aberrations detected

A wearable ECG sensor like SEP can flex during use as the wearer moves and this can lead to two types of signal artifacts: (a) signal aberrations caused when one or both electrodes momentarily lose connection with the body, a situation called "leads-off", and (b) when motion causes the captured signal contents to be distorted through the introduction of false peaks and crests. In either case, these signal artifacts need to be detected and rejected before heart rate and heart rate variability calculations are resumed. Appropriate error signals are sent to the host device. The motion artifact detection technique implemented within the SEP (that is, on-board) is as follows. FIGS. 4A and 4B show the leads-off and motion/noise artifacts detected when SEP is on a human subject The ADT uses a technique called dynamic baseline matching which maintains the average value of the captured ECG signal within a moving window that advances with each ECG period. If the baseline calculated for the most recent period deviates significantly from the average calculated for the window, a leads-off condition is detected within the last period of measurement and the moving average is not updated with data from the current period and the window is simply moved forward by one period. If the leads-off condition is not detected, the moving average is updated, and the window is moved forward. By maintaining a dynamic window, natural variations in the ECG pattern caused by sweating and normal temporal changes caused by slow motion are allowed for.

When either motion/noise artifact or leads off is detected the MPT in software momentarily suspends data processing, and resets all thresholds, buffers, and baseline while it waits for a good ECG signal to resume processing. It recomputes the ECG baseline, and MPT goes through pre-processing again to reestablish the baseline. If noise, or leads off signal lasts for over 2 seconds, it loops in pre-processing until there's a true R-peak detected. Extended periods of useful signal acquisition losses trigger the transmission of an error code to the host for notification/intervention.

The ADT monitors the baseline consistency, running at a frequency of 10 Hz in parallel with the MPT. After the pre-preprocessing phase, the MPT processes each sample in the ECG signal in two steps: First, it monitors for real-time slope change in the input ECG signal. For every transition of the signal's slope from positive to negative (implying a potential R-peak), followed by a transition from a negative slope to a positive slope (implying a potential S-peak) it records the peak as a potential R-peak in a Peak Buffer (PB) in memory. The PB, e.g., size of 4 bytes, can hold two values where one value is the true R-Peak, and the second value is the potential R-peak which is compared with the true R-peak to determine if it is a true R-peak. If the comparison returns "True" then the most recent true R-peak is stored in the buffer, and the R-peak preceding it is deleted from the buffer to make place for the next potential R-peak. The acquired signal for a single period is considered as a motion artifact and unacceptable if any one of the following conditions are true:

a. The detected R-peak's amplitude is not within $\pm\Delta R$ of the last measured baseline from accepted signals. This threshold ($\Delta R$) is also configurable. Any signal peak outside this range is considered as a motion artifact. For the implementation presented here, $\Delta R$ is 30% above/below the most recently estimated baseline average. It is to be noted that this threshold value is empirical and determined from an analysis of the archived signals in the Massachusetts Institute of Technology-Beth Israel Hospital Arrhythmia Database (MIT BIH Database, physionet.org/content/mitdb/1.0.0/) (as well as actual measurements on subjects).

b. The potential R-peak is a high-frequency signal peak, with inter-peak distances less than the highest expected heart rate (240 bpm), that is with inter-peak distances of less than 250 mS and peak amplitudes less than 10% of the running baseline average for accepted signals. These potential R-peaks are ignored as high frequency noise.

c. The potential R-peak implies a heartbeat rate outside an expected heartbeat range of 30 to 240 bpm (beats per minute), corresponding to R-to-R peak intervals of 2000 and 250 mS, respectively. The peaks meeting this criterion are considered as induced by motion artifacts. Again, this range of acceptable heartbeat rates is pre-configurable.

This implementation uses independent threads to detect the rejection conditions for R-peaks mentioned under (a) through (c) above. When acceptable signals are identified, the baseline is estimated by averaging consistent acceptable signals over the past two seconds without the accepted R-peak and the Q-peak that follows it. Leads-off conditions indicating signals that need to be also rejected are identified as follows: (i) The acquired signal's R-peak within a 2 second interval is over 30% of the value of the R-peak baseline of accepted signals or if the acquired signal has saturated at the highest possible acquired signal value, or (ii) The acquired signal's peak value over the 2-second interval is between the least possible signal value and less than 30% of the baseline. If the period of two potential peaks is greater than the period-threshold, then the MPT regards the input signal as an ECG R-peak and calculates the instantaneous heart rate. MPT maintains a global counter, which counts every sample processed. This counter helps to determine the period between consecutive R-peaks and helps to calculate the instantaneous heart rate. This technique has low complexity compared to other peak detection techniques such as the one described in [27] which are not practical to implement in an onboard processing system like SEP.

Figure 5A:
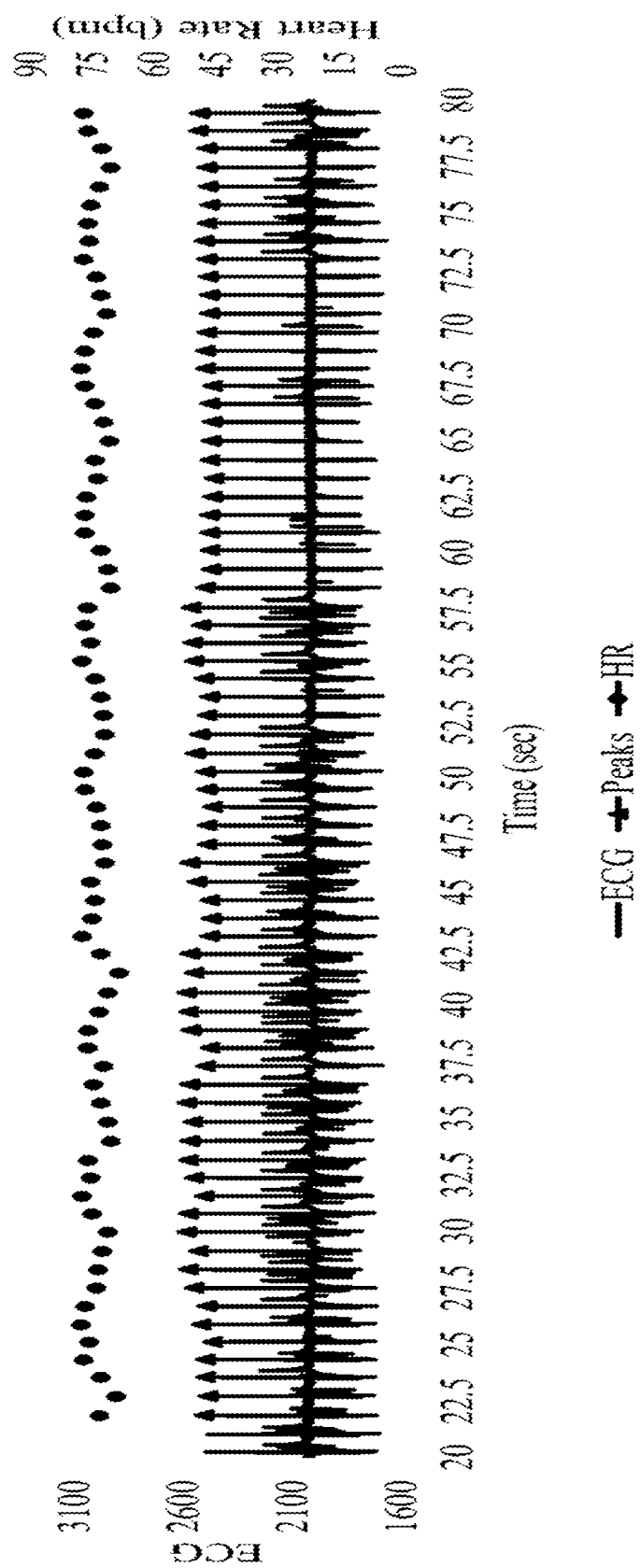
FIG. 5A shows an MIT-BIH ECG signal. R-peak detection, and Heart rate calculation are performed onboard the SEP, processed on MIT-100 ECG signal

In FIG. 5A, detected R-peaks, instantaneous heart rate computed by SEP's MPT is shown as it was seen on the Bluetooth host.

Figure 5B:
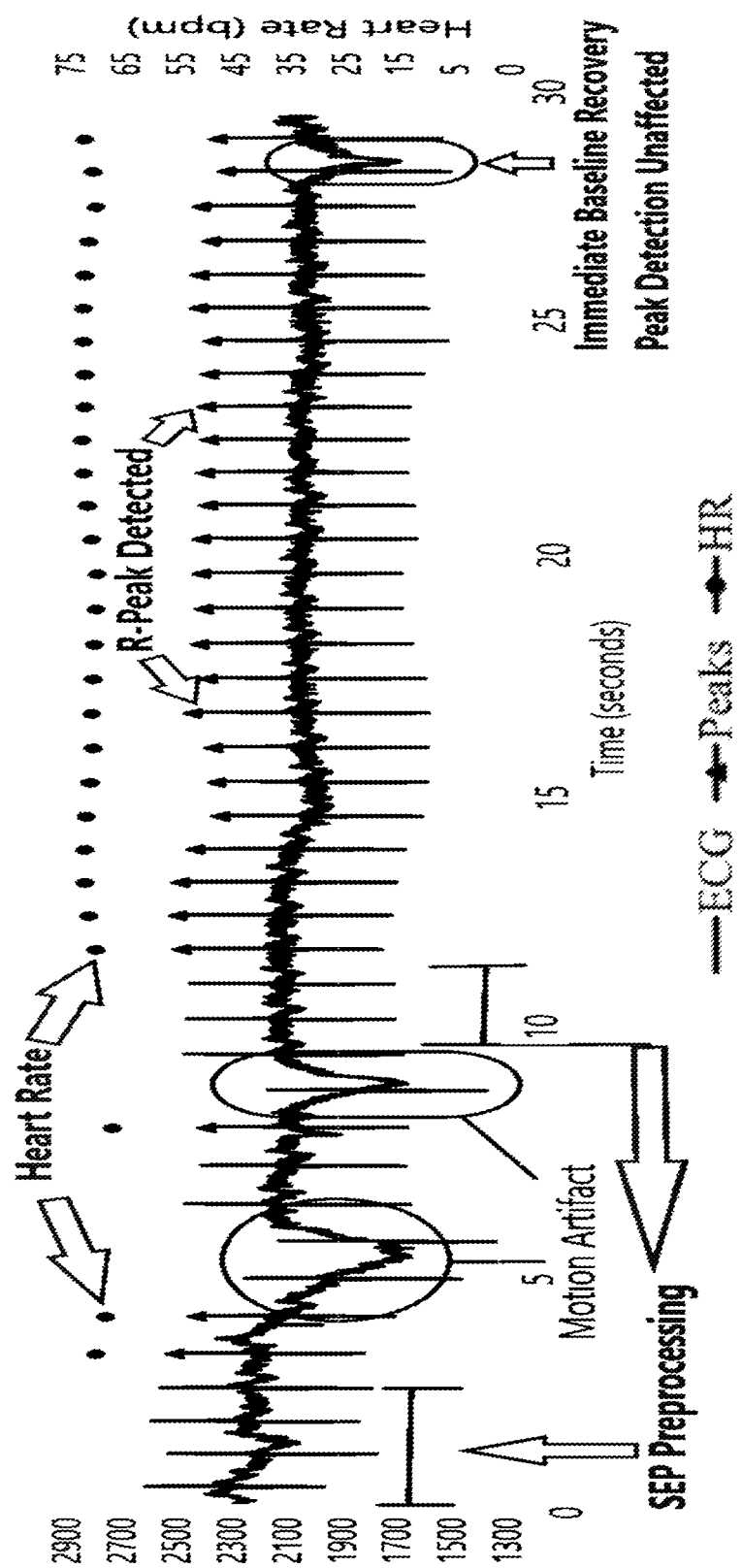
FIG. 5B shows a human subject ECG signal. R-peak detection, and Heart rate calculation are performed onboard the SEP, processed on the ECG signal from Human Subject. The y-axis on the left represents the digitized ECG signal amplitude. The y-axis to the right represents the instantaneous heart rate (HR) (dots). R-peaks are detected and represented by a triangular marker

In FIG. 5B, MPT detects all R-peaks, instantaneous heart rate, and motion artifacts (detected by ADT) in the ECG signal from a human subject. (Appropriate IRB protocols were in place.) For this experiment, the SEP continuously transmitted data to the host in real-time at a 100% duty cycle.

The definition and classification of heart rate variability parameters is given in [16]. Onboard the SEP, four short-term time-domain heart rate variability parameters are estimated, and buffered on a limited flash memory of 128 KB. Average of all NN intervals (AVNN), Standard Deviation of all NN intervals (SDNN), Square root of the mean of squares of differences between adjacent NN intervals (RMSSD), Percentage of differences between adjacent NN intervals that are greater than 50 mS (pNN50) are the four heart rate variability parameters estimated onboard SEP. Instantaneous heart rate is buffered in memory every 5 minutes. Maximum size of this buffer is 1200 Bytes, and this buffer can thus hold 1200 instantaneous heart rate values. The buffer is reset and cleared at the end of 5-minute interval after the heart rate variability parameters are estimated.

The heart rate variability parameters estimated by the SEP are compared with the heart rate variability parameters estimated by Shimmer [17], and BioSPPy [3] on the same ECG signal. To do this, the SEP transmits the instantaneous heart rate at 100% duty cycle to the connected Bluetooth Host. All the incoming instantaneous heart rate is buffered on the host, it runs two threads, one runs the Shimmer heart rate variability computation, and other runs BioSPPy heart rate variability computation. The ECG signals used to estimate the heart rate variability parameters are sourced from the MIT-BIH database, and from human subjects.

SEP uses wireless Bluetooth Low Energy (BLE) protocol [5] to communicate over Bluetooth radio. The onboard software (TT and RT) uses BLE protocol stack API (Application Program Interface) for its communication purposes. The SEP's software application runs on top of a Generic Access Protocol (GAP) layer, and a Generic Attribute Profile (GATT) layer which are part of the Bluetooth Low Energy (BLE) protocol stack.

The SEP transmits five different types of data over BLE to a connected Bluetooth host. Each ECG data sample, whose value ranges from 0-4095, is of the size 2 Bytes, communicated over BLE in stream of 20 Byte (Payload size) packets. The transmission frequency depends on the duty cycle that the SEP is set to operate. Next, the instantaneous heart rate data is computed by the SEP in terms of beats-per-minute (bpm), ranging between 0-240, of size 1 Byte, and a packet payload of 1 Byte. The transmission frequency depends on the SEP's duty cycle. An alarm signal is sent to the Bluetooth host by the SEP upon successful detection of noise/motion artifact in the incoming signal. This is a Boolean value and is transmitted only when its value is "True". The heart rate variability parameters data computed by the SEP is a one-time transmission at the end of each 5-minute time interval. Three heart rate variability parameters are expressed in milliseconds and only pNN50 is expressed as a percentage. The packet payload size for heart rate variability parameters is 8 Bytes. The SEP also communicates its battery level to the Bluetooth host when there is a drop in its value by 1%.

To ensure a secure connection and mitigate eavesdroppers, brute force key attacks, and other security breaches, the SEP's MCU implements Elliptic Curve Cryptographic (ECC) algorithm stored in its Read-Only Memory (ROM). The use of ECC combined with a hardware-based true random number generator ensures that the key generated is resistant against the security attacks. In addition, the SEP uses a randomly generated Bluetooth device address in its advertising mode. The random address is derived from a cryptographic function and it changes periodically, typically every 15 minutes. Only after a secure connection is setup with a trusted host device, is the SEP's real Bluetooth device address disclosed along with an Identity Resolving Key (IRK). This way, untrusted devices, who do not have an IRK, will have no way of tracking advertisements from the SEP, thereby the SEP's real Bluetooth device address cannot be resolved for malicious purposes. Further, all packets in-between the SEP and its hosts are encrypted using AES-128 using 16 Byte (128 bit) keys to protect the sensitive data and wearer's privacy.

Four short-term time domain HRV parameters [16] are computed on board of SEP at 5-minute time intervals. The SEP has a limited in-System flash memory of 128 KB, thus, short term HRV is estimated onboard. Long term HRV (over a 24-hour period) are computed on Bluetooth Host side. The SEP acquired and processed ECG signal from the MIT-100 certified ECG signal database and human subjects. BioSPPy [3], an ECG toolbox developed in python, was used to do a comparative study of SEP's HRV computation accuracy.

The technology reduces the total power consumption, thereby significantly improving endurance on a single coin battery. The SEP is powered, for example, by a CR2032 coin battery (3V, $LiMnO_2$, 235 mAH), which is a balanced tradeoff between the physical dimensions of the SEP and operation time on the battery. The most dominant source of energy consumption is in the Bluetooth communication with the host. SEP uses a variety of techniques to reduce its power consumption, ranging from transmission power adjustment to actually curbing transmission adaptively based on real-time acquisition and processing of ECG signals on-board.

One way to reduce this power is to reduce the transmission power [22] from the SEP from +5 dBm to −21 dBm. The required transmission power is a function of the proximity of the host to the SEP. At the lowest transmission power level (−21 dBm), the host proximity is limited to 1 to 3 meters, due to ambient conditions. SEP determines the desired transmit power at connection setup time by reading the value of Received Signal Strength Indicator (RSSI) obtained from the Bluetooth radio interface. The RSSI depends on the ambient conditions, distance between the SEP and the host and ambient signal interference.

Beyond the modulation of transmission power, additional power operating modes were developed onboard the SEP to operate at a duty cycle less than 100% to progressively reduce the operating power, extending the longevity of the battery life through adaptive transmission. The host device sends a command packet to the SEP to specify these operation modes. The duty cycle is expressed as a percentage of the time duration for which the SEP is active (sum of the duration of all active periods in which data acquisition, its on-board processing/analysis and continuous transmission takes place) divided by the total running time of the SEP (sum of all active and inactive periods). For the results related to power consumption, an 8 mV peak-to-peak synthetic ECG signal derived from the MIT-BIH database traces was used to drive SEP. This was done to produce consistent results in a controlled manner.

In decreasing order of operating power, the SEP power (and operation) modes are as follows:

A. Continuous Transmission Mode (CONT)

The SEP captures, processes and sends the ECG signal, heart rate and heart rate variability to the host continuously. The heart rate and heart rate variability data are interspersed with ECG data every minute. The heart rate variability data represents the results collected in the past 5 minutes, while heart rate is instantaneous heart rate computed whenever a R-peak is detected. The battery life is minimum and is determined by the specified transmission power level.

B. Simple Duty Cycling (SD) Power Mode

The SEP uses host-dictated duty cycle management technique to ensure that overall average current draw is kept lower than in the CONT transmission mode. In this mode, the SEP operates continuously for 5 minutes (independent of the duty cycle specified) in the CONT mode and then goes to sleep in the lowest power mode possible for time specified by the duty cycle. For instance, when the duty cycle specified is 40% (that is operate for 40% of a cycle and sleep for 60% of the cycle time), the SEP operates in the CONT mode for 5 minutes and then goes to sleep for 7.5 minutes. During the sleep phase, the processing of signals from ECG electrodes, motion artifact/noise removal, peak detection, heart rate/heart rate variability estimation, and transmission to the host are all suspended. On wakeup via a timer interrupt from the sleep phase, SEP notifies its presence to the host and reconnects to it and then resumes operation in the CONT mode for the next active phase for 5 minutes.

Figure 6:
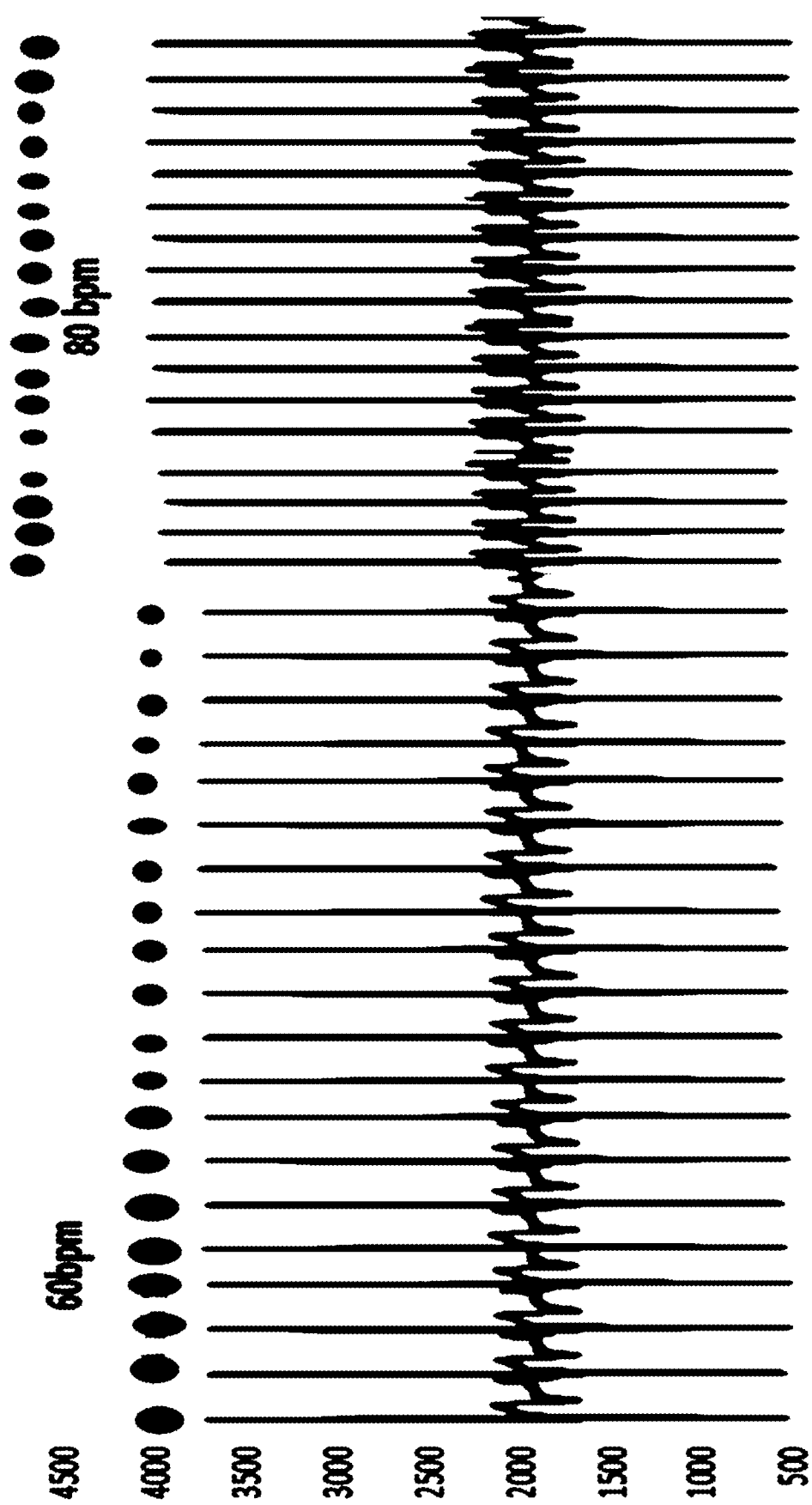
FIG. 6 shows an ECG tracing with an abrupt change in heart rate from 60 bpm to 80 bpm, with the dots showing the rate change rapidly tracked.

FIG. 6 shows an ECG tracing with an abrupt change in heart rate from 60 bmp to 70 bmp. The dots above the ECG reflect recognition of the heartbeat, and show that the SEP tracks the change rapidly.

Figure 7:
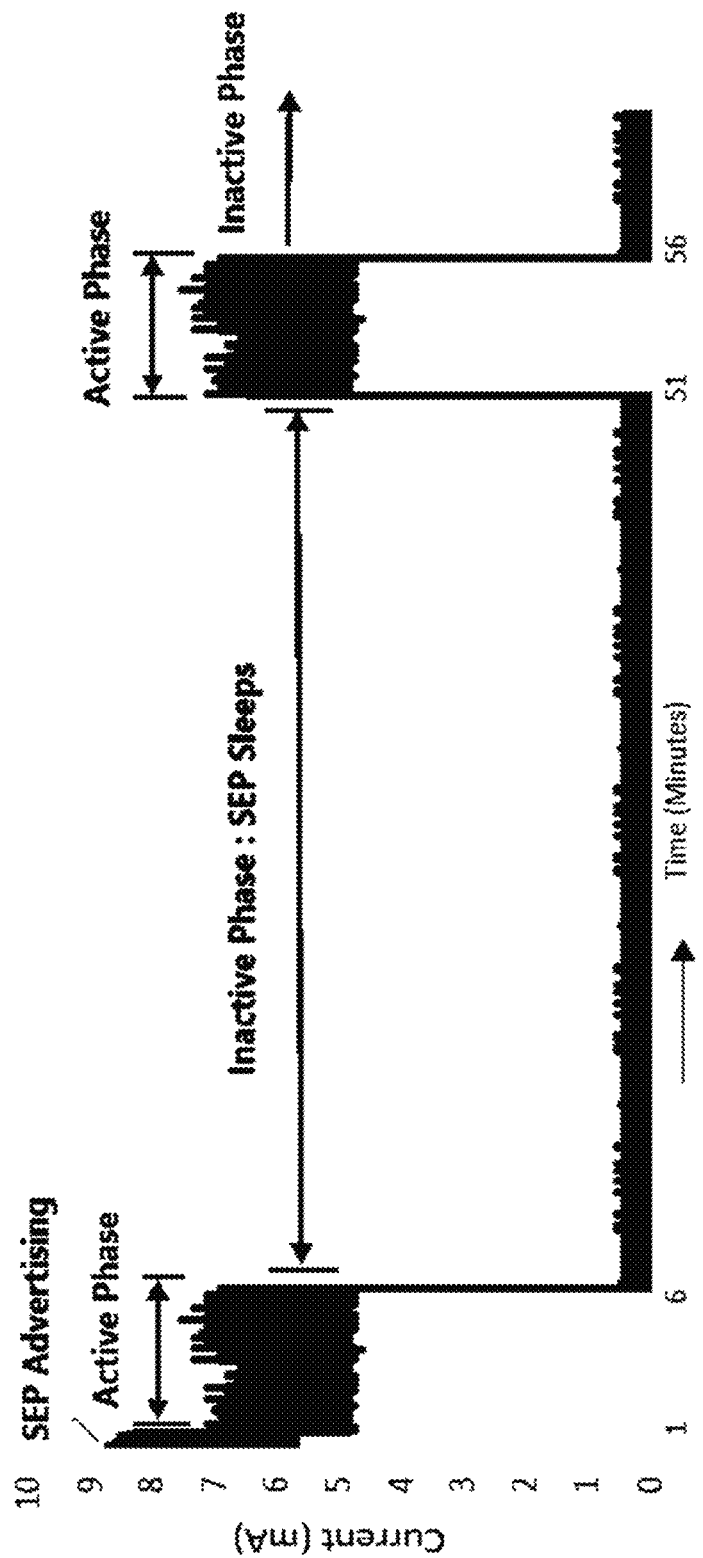
FIG. 7 shows both ECG and heart rate transmissions and power consumed by SEP operating in AD-CHR+TE power mode at a Simple 10% Duty cycling seen on a Bluetooth host device during an active period.

ECG, heart rate transmission, and the current drawn by SEP is shown in FIG. 7. The power savings in this mode comes from keeping the SEP inactive during the quiescent period, e.g., 90% of the time, and transmitting only during a 10% on duty cycle. However, nothing is done within the active phase to save power in this operation mode.

C. Adaptive Duty Cycling with Continuous Heart Rate Transmission and Triggered ECG Transmission (AD-CHR+TE) Power Mode In a mode triggered by HR variation (A-ECG), the transmission of the ECG data is done adaptively during the active phase of the duty cycle. The instantaneous heart rate payload is only one Byte long and needs to be transmitted only when a new R-peak is detected by the SEP's MPT. The instantaneous heart rate transmission, compared to the ECG data transmission, saves transmission energy because of its small payload size and lower transmission rate. This mode is similar to the DC mode, but: (a) only the instantaneous heart rate is transmitted during the active phase, followed by the heart rate variability at the end of the active phase if the heart rate stays within a threshold; (b) heart rate, heart rate variability and the ECG waveforms are sent to the host during the active part only when the heart rate falls outside the threshold. The threshold is 10% of the estimated instantaneous heart rate on either side of the running average heart rate.

In the A-ECG mode, the heart rate variability parameters are transmitted at the end of the 5-minute active period just as in the previous power mode. Note that in this mode, the heart rate variability parameters are computed onboard the SEP from all ECG data collected during the past 5-minute active period even when it's not transmitted to the host. Compared to the SD mode, if the heart rate stays within the specified range, the power savings are realized by not transmitting the ECG waveform during the active phase.

Another scenario where the transmissions are limited/restricted is when the ADT detects either a motion/noise artifact, or a leads-off condition. In these cases, an alarm signal is sent to the connected Bluetooth host device so that the host/user is made aware of the situation. Also, all transmissions are paused until a good ECG signal is seen at the input of the SEP electrodes.

Figure 8:
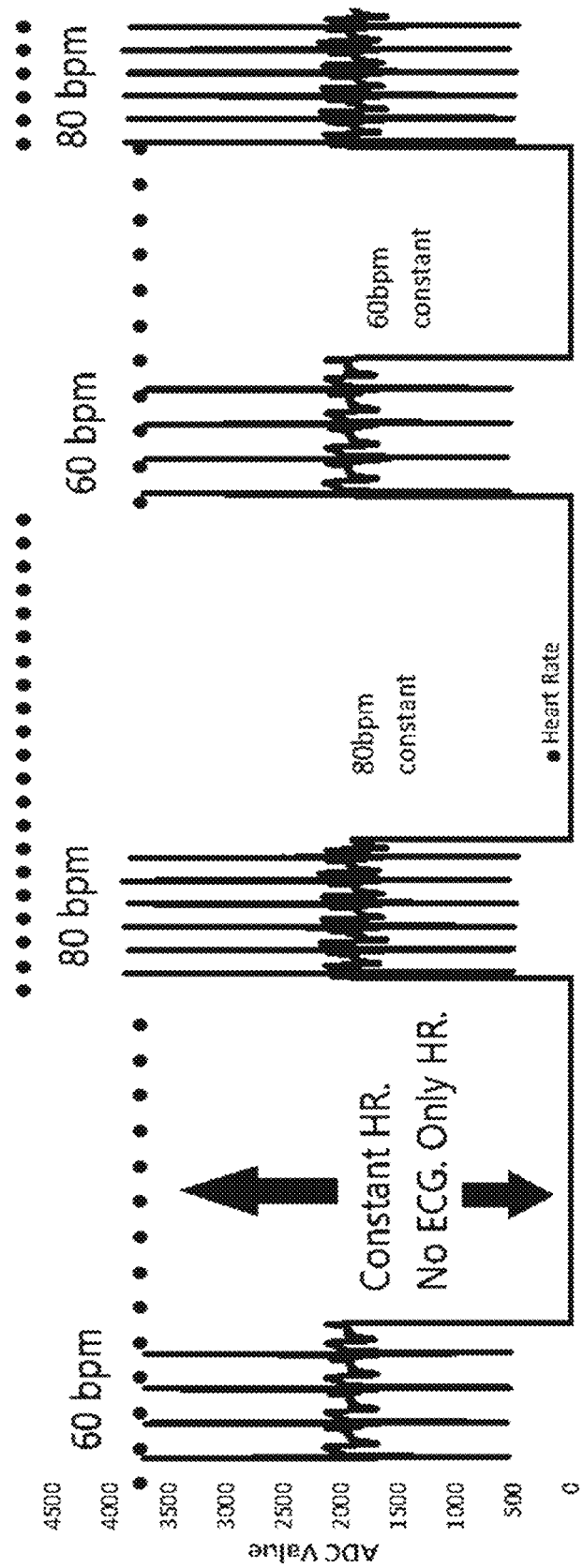
FIG. 8 shows heart rate and ECG signals transmissions and power consumed as seen on Bluetooth host device during an active period in AD-CHR+TE power mode. Heart rate is marked with dots.

As shown in FIG. 8, ECG and heart rate transmission are shown as displayed on a Bluetooth host, and current drawn by SEP in this phase is plotted in FIG. 7. The power savings are exploited in cases when the human subject is at rest, or performing a physical activity at almost constant rate, for example, walking at almost constant pace.

D. Adaptive Duty Cycling with Triggered Heart Rate and ECG Transmission (AD-TR+TE) Power Mode This mode extends power savings further beyond the previous mode (AD-CHR+TE) by not sending any heart rate, heart rate variability or ECG signal to the host during the active phase if the heart rate stays within the heart rate threshold. In lieu of these signals, a keep-alive signal is sent to the host to inform that the SEP is operating properly even though it has not sent the heart rate, heart rate variability and ECG signals. The heart rate threshold is same as described for the previous mode. This power mode of operation is the most aggressive, power-efficient, and conservative mode of the SEP software. It realizes the highest power savings among the operation modes described. All true detections of either a motion/noise artifact or leads off condition are handled as described previously. Characteristics of inactive period in this operating mode are the same as the one described in previous power mode.

Figure 9:
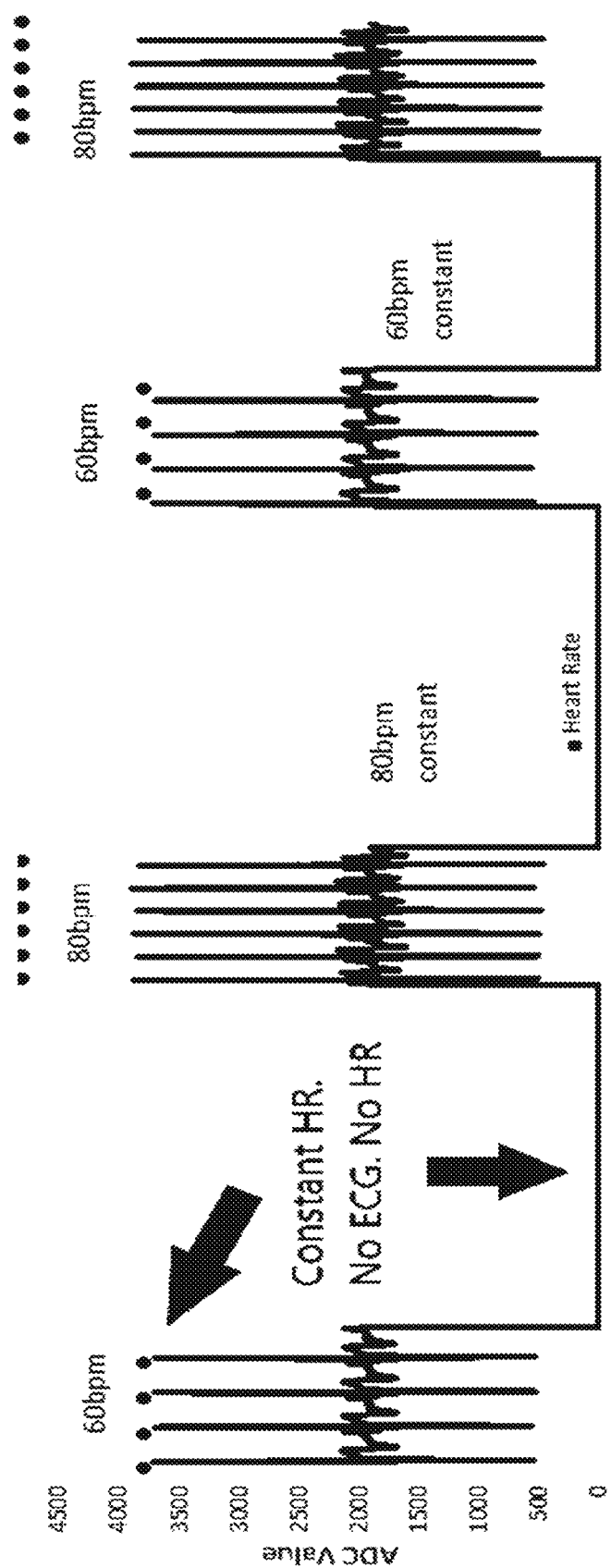
FIG. 9 shows ECG and heart rate transmissions and power consumed in AD-TR+TE power mode as seen on host device interface during an active period. Heart rate is marked with dots.

In FIG. 9, ECG and heart rate transmission received by the Bluetooth host is shown.

Figure 10:
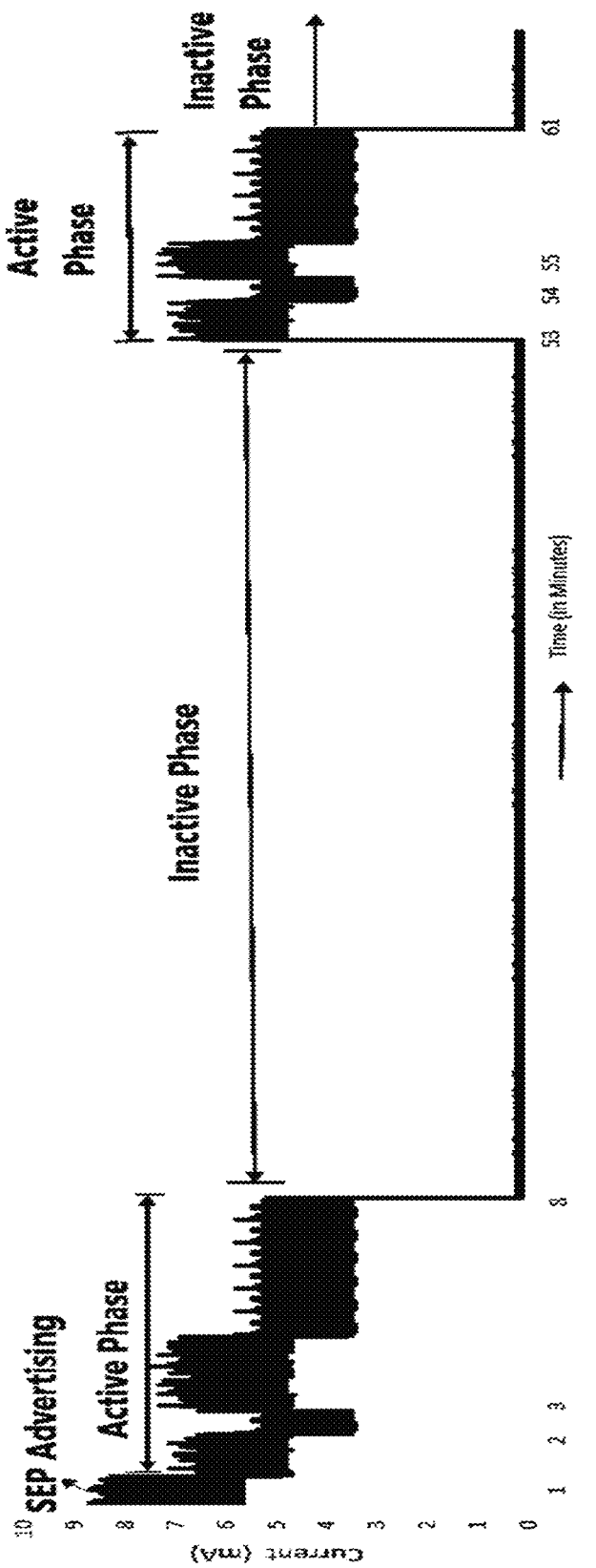
FIG. 10 shows the electrical current drawn by SEP in AD-TR+TE power mode at 10% duty cycle.

In FIG. 10, current drawn by SEP in this power mode is plotted.

The SEP's power consumption in the normal mode and the various power-conserving modes, was measured using a National Instruments (NI) USB-6259 Data Acquisition Module with NI LabVIEW Software Application based on the voltage drop across a small resistor (1.5 Ohms) in series with the SEP's battery. The battery life was measured as the time from the moment a SEP was turned on (with a fresh battery) to the time the battery voltage dropped below 1.8 V (the operating range for TI CC2640 is 1.8 V-3.8 V). The battery life is determined at three operating duty cycles: 10%, 50%, and 100%.

Table 1 shows the average battery current during active phase when the SEP transmits at a specific duty cycle. It also shows the average current consumption during inactive mode of the duty cycle in each of the three duty cycle modes. The right-most column in this table shows the battery life, in hours, noted at three duty cycles. A set of three SEPs were used for the battery life measurements; All had one CR2032 coin cell battery each. Each set of SEP was operated at the three duty cycles, with each run using a new coin battery. The battery life for these three duty cycle modes was determined as the average battery life seen with each of the three SEPs by allowing the SEP to drain the battery to its fullest until SEP disconnects the BLE connection to the host (at a battery voltage of 1.8 Volts) and turns off. The number of operating hours were noted for these duty cycle operation modes. With the SEP software's duty cycle management for power saving, peak detection and BLE radio on the battery lasts on the average at least 27.8 hours at 100% duty cycle, 54.9 hours at 50% duty cycle, and 249.6 hours at 10% duty cycle. Table 1 summarizes these results.

TABLE 1

SUMMARY OF BATTERY LIFE ESTIMATION
FOR SEP AT DIFFERENT DUTY CYCLES

| Duty Cycle (%) | Active Period | | Inactive Period | | Total | Battery CR2032 | |
|---|---|---|---|---|---|---|---|
| | Avg Current (mA) | Time (s) | Avg Current (mA) | Time (s) | Average Current (mA) | Capacity (mAh) | Battery Life (hours) |
| 100 | 5.54 | 3600 | 0.07 | 0 | 5.54 | 220 | 27.8 |
| 50 | 5.54 | 1800 | 0.07 | 1800 | 2.80 | 220 | 55.0 |
| 10 | 5.54 | 360 | 0.07 | 3240 | 0.62 | 220 | 249.6 |

The Smart ECG Patch (SEP) is a self-contained ECG sensor that successfully performed all critical processing on-board. Specifically, it detected and corrected for signal artifacts, including motion artifacts, that enabled the accurate estimation of the heart rate and heart rate variability parameters of the wearer. The SEP also implements low power operating modes that prolong its operating time significantly by trading off between optimized functionality and overall power consumption. ECG signals from the archived MIT-BIH database and human subjects wearing the SEP were used to verify all aspects of the SEP's operation, signal analysis, data transmission and power savings.

Further enhancements to the design provide a form factor of 1.25 by 2 inches, 16-bit analog to digital signal acquisition, further reductions in energy consumption, and use of a flexible rechargeable battery (rather than a metal coin cell).

The ability to perform onboard signal analysis was important for generating alarms reliably based on continuously-monitored wearer conditions and for realizing a very long battery life using adaptive transmissions of heart rate and heart rate variability signals.

The SEP may have dimensions of 1.25 inches by 2 inches (with the longer dimension related to the required electrode separation for ECG signal acquisition), and may uses a small rechargeable battery instead of the primary lithium battery, and a 16-bit ADC and may employ more sophisticated onboard processing, and analysis of ECG signal, while realizing a long battery life. The rechargeable battery may be associated with an energy harvesting system. For example, the battery may be recharged by a photovoltaic cell, an inductive coil for RF energy harvesting, a magnet moving with respect to a coil to harvest mechanical energy, or other known types of energy harvesting systems.

Machine learning techniques may be used estimate the various rejection thresholds and rejection intervals to make them specific to subjects and specific to types of movements.

REFERENCES (EACH REFERENCE CITED
HEREIN IS EXPRESSLY INCORPORATED
HEREIN BY REFERENCE FOR ALL
PURPOSES)

[1] Akrivopoulos, Orestis, et al. "Design and Evaluation of a Person-Centric Heart Monitoring System over Fog Computing Infrastructure." Proceedings of the First International Workshop on Human-centered Sensing, Networking, and Systems. ACM, 2017.

[2] "CALM-M Class I Medical Device for Hospitals and Home Care." CALM. www.calm-health.com/calm-healthcare/.

[3] Carreiras, C., et al. "BioSPPy: Biosignal processing in Python." Accessed on 3.28 (2015): 2018.

[4] Coulter, Simon, et al. "Low power IoT platform for vital signs monitoring." Signals and Systems Conference (ISSC), 2017 28th Irish. IEEE, 2017.

[5] Gomez, C., Oller, J., & Paradells, J. (2012). Overview and evaluation of bluetooth low energy: An emerging low-power wireless technology. Sensors, 12(9), 11734-11753.

[6] Jani, Abhishek B., Ravi Bagree, and Anil K. Roy. "Design of a low-power, low-cost ECG & EMG sensor for wearable biometric and medical application." SENSORS, 2017 IEEE. IEEE, 2017.

[7] Jin-ling, Zhang, et al. "An ECG 7-lead monitoring system designing based on lower-power." Complex Medical Engineering (CME), 2013 ICME International Conference on. IEEE, 2013.

[8] Khalaf, Abdelbaset, and Rishaad Abdoola. "Wireless body sensor network and ECG Android application for eHealth." Advances in Biomedical Engineering (ICABME), 2017 Fourth International Conference on. IEEE, 2017.

[9] Krachunov, Sammy, et al. "Energy efficient heart rate sensing using a painted electrode ECG wearable." Global Internet of Things Summit (GIoTS), 2017. IEEE, 2017.

[10] Miao, Fen, et al. "A wearable context-aware ECG monitoring system integrated with built-in kinematic sensors of the smartphone." Sensors 15.5 (2015): 11465-11484.

[11] Nemati, Ebrahim, M. Jamal Deen, and Tapas Mondal. "A wireless wearable ECG sensor for long-term applications." IEEE Communications Magazine 50.1 (2012).

[12] Park, Chulsung, et al. "An ultra-wearable, wireless, low power ECG monitoring system." Biomedical Circuits and Systems Conference, 2006. BioCAS 2006. IEEE. IEEE, 2006.

[13] Poliks, Mark, et al. "A wearable flexible hybrid electronics ECG monitor." Electronic Components and Technology Conference (ECTC), 2016 IEEE 66th. IEEE, 2016.

[14] Ra, Ho-Kyeong, et al. "I am a Smart watch, Smart Enough to Know the Accuracy of My Own Heart Rate Sensor." Proceedings of the 18th International Workshop on Mobile Computing Systems and Applications. ACM, 2017.

[15] Sen-Gupta, Ellora, Donald E. Wright, James W. Caccese, John A. Wright Jr, Elise Jortberg, Viprali Bhatkar, Melissa Ceruolo et al. "A Pivotal Study to Validate the Performance of a Novel Wearable Sensor and System for Biometric Monitoring in Clinical and Remote Environments." Digital Biomarkers 3, no. 1 (2019): 1-13.

[16] Shaffer, Fred, and J. P. Ginsberg. "An overview of heart rate variability metrics and norms." Frontiers in public health 5 (2017): 258.

[17] Shimmer3 ECG Unit. (n.d.). Retrieved from www.shimmersensing.com/products/shimmer3-ecg-sensor

[18] Shin, Seung-chul, et al. "Two electrode based healthcare device for continuously monitoring ECG and BIA signals." Biomedical & Health Informatics (BHI), 2018 IEEE EMBS International Conference on. IEEE, 2018.

[19] Sylvester, S. S., et al. "Miniaturized and Wearable Electrocardiogram (ECG) Device with Wireless Transmission." Journal of Telecommunication, Electronic and Computer Engineering (JTEC) 9.3-9 (2017): 15-19.

[20] Jovin, I., Maslakovic, M., Maslakovic, M., Johnson, D., Jovin, I., Maslakovic, M., . . . Jovin, I. (2019, Apr. 28). Keep tabs on your heart: Wearables that come with an ECG sensor. Retrieved from gadgetsandwearables.com/2018/09/22/ecg-sensor/

[21] Wang, hanging, et al. "Wearable ECG Based on Impulse-Radio-Type Human Body Communication." IEEE Trans. Biomed. Engineering 63.9 (2016): 1887-1894.

[22] Wang, Yishan, et al. "A wearable wireless ECG monitoring system with dynamic transmission power control for long-term homecare." Journal of medical systems 39.3 (2015): 35.

[23] Yang, Zhe, et al. "An IoT-cloud based wearable ECG monitoring system for smart healthcare." Journal of medical systems 40.12 (2016): 286.

[24] Baig, Mirza Mansoor, Hamid Gholamhosseini, and Martin J. Connolly. "A comprehensive survey of wearable and wireless ECG monitoring systems for older adults." Medical & biological engineering & computing 51.5 (2013): 485-495.

[25] Huang, Hui, Shiyan Hu, and Ye Sun. "Energy-efficient ECG compression in wearable body sensor network by leveraging empirical mode decomposition." Biomedical & Health Informatics (BHI), 2018 IEEE EMBS International Conference on. IEEE, 2018.

[26] Islam, S M Riazul, et al. "The internet of things for health care: a comprehensive survey." IEEE Access 3 (2015): 678-708.

[27] Pan, Jiapu, and Willis J. Tompkins. "A real-time QRS detection algorithm." IEEE transactions on biomedical engineering 3 (1985): 230-236.

[28] Wang, Robert, et al. "Accuracy of wrist-worn heart rate monitors." Jama cardiology 2.1 (2017): 104-106.

[29] Gusev, Marjan, and Ana Guseva. "State-of-the-art of cloud solutions based on ECG sensors." Smart Technologies, IEEE EUROCON 2017-17th International Conference on. IEEE, 2017.

[30] Fensli, Rune, Einar Gunnarson, and Torstein Gundersen. "A wearable ECG-recording system for continuous arrhythmia monitoring in a wireless tele-home-care situation." Computer-Based Medical Systems, 2005. Proceedings. 18th IEEE Symposium on. IEEE, 2005.

[31] Anliker, Urs, et al. "AMON: a wearable multiparameter medical monitoring and alert system." IEEE Transactions on information technology in Biomedicine 8.4 (2004): 415-427.

[32] Yang, Geng, et al. "A novel wearable ECG monitoring system based on active-cable and intelligent electrodes." e-health Networking, Applications and Services, 2008. HealthCom 2008. 10th International Conference on. IEEE, 2008.

[33] Spanó, Elisa, Stefano Di Pascoli, and Giuseppe Iannaccone. "Low-power wearable ECG monitoring system for multiple-patient remote monitoring." IEEE Sensors Journal 16.13 (2016): 5452-5462.

[34] Soh, Ping Jack, et al. "Wearable wireless health monitoring: Current developments, challenges, and future trends." IEEE Microwave Magazine 16.4 (2015): 55-70.

[35] Chowdhury, Muhammad E H, et al. "Wearable Real-Time Heart Attack Detection and Warning System to Reduce Car Accidents in Qatar." Qatar Foundation Annual Research Conference Proceedings. Vol. 2018. No. 2. Qatar: HBKU Press, 2018.

[36] Lobodzinski, S. Suave, and Michael M. Laks. "New devices for very long-term ECG monitoring." Cardiology journal 19.2 (2012): 210-214.

[37] Chlaihawi, Amer Abdulmandi, et al. "Development of printed and flexible dry ECG electrodes." Sensing and Bio-Sensing Research (2018).

[38] Baba, Elhoussaine, Abdelillah Jilbab, and Ahmed Hammouch. "A health remote monitoring application based on wireless body area networks." Intelligent Systems and Computer Vision (ISCV), 2018 International Conference on. IEEE, 2018.

[39] Jang, Do-Hun, and SeongHwan Cho. "A 43.4 µW photoplethysmogram-based heart-rate sensor using heartbeat-locked loop." Solid-State Circuits Conference-(ISSCC), 2018 IEEE International. IEEE, 2018.

[40] Khan, Yasser, et al. "Flexible Hybrid electronics: direct interfacing of soft and hard electronics for wearable health monitoring." Advanced Functional Materials 26.47 (2016): 8764-8775.

[41] Shin, Seung-chul, et al. "Two electrode based healthcare device for continuously monitoring ECG and BIA signals." Biomedical & Health Informatics (BHI), 2018 IEEE EMBS International Conference on. IEEE, 2018.

[42] Coulter, Simon, et al. "Low power IoT platform for vital signs monitoring." Signals and Systems Conference (ISSC), 2017 28th Irish. IEEE, 2017.

[43] Nemati, Ebrahim, M. Jamal Deen, and Tapas Mondal. "A wireless wearable ECG sensor for long-term applications." IEEE Communications Magazine 50.1 (2012).

[44] Khalaf, Abdelbaset, and Rishaad Abdoola. "Wireless body sensor network and ECG Android application for eHealth." Advances in Biomedical Engineering (ICABME), 2017 Fourth International Conference on. IEEE, 2017.

[45] Jani, Abhishek B., Ravi Bagree, and Anil K. Roy. "Design of a low-power, low-cost ECG & EMG sensor for wearable biometric and medical application." SENSORS, 2017 IEEE. IEEE, 2017.

[46] Krachunov, Sammy, et al. "Energy efficient heart rate sensing using a painted electrode ECG wearable." Global Internet of Things Summit (GIoTS), 2017. IEEE, 2017.

[47] Wang, hanging, et al. "Wearable ECG Based on Impulse-Radio-Type Human Body Communication." IEEE Trans. Biomed. Engineering 63.9 (2016): 1887-1894.

[48] Wang, Yishan, et al. "A wearable wireless ECG monitoring system with dynamic transmission power control for long-term homecare." Journal of medical systems 39.3 (2015): 35.

[49] Sylvester, S. S., et al. "Miniaturized and Wearable Electrocardiogram (ECG) Device with Wireless Transmission." Journal of Telecommunication, Electronic and Computer Engineering (JTEC) 9.3-9 (2017): 15-19.

[50] Welch Allyn Inc., TAGecg brochure, October 2018.

[51] V. Randazzo, J. Ferretti and E. Pasero, "ECG WATCH: a real time wireless wearable ECG," 2019 IEEE International Symposium on Medical Measurements and Applications (MeMeA), Istanbul, Turkey, 2019, pp. 1-6. doi: 10.1109/MeMeA.2019.8802210

[52] De Capua, Claudio, Antonella Meduri, and Rosario Morello. "A smart ECG measurement system based on web-service-oriented architecture for telemedicine applications." IEEE Transactions on Instrumentation and Measurement 59.10 (2010): 2530-2538.

[53] Ali, Hassan, Ben Ernest Villaneouva, and Raziq Yaqub. "Design and Implementation of a Low Cost Wireless Ambulatory ECG Monitoring System for Deployment in Rural Communities." International Journal of Online and Biomedical Engineering (iJOE) 15, no. 15 (2019): 57-79.

[54] Baheti, Ashutosh, Anshul Jain, Yamini Goyal, and Amit Neogi. "Bluetooth Controlled Life Savior System."

[55] Benade, S. A., and U. L. Bombale. "FINGER TOUCH BASED ECG MONITORING." IJRET: International Journal of Research in Engineering and Technology eISSN: 2319-1163|pISSN: 2321-7308, Volume: 05 Issue: 07|July-2016, ijret.esatjournals.org

[56] Bhamra, Hansraj Singh. "Micro-power circuits and systems for wireless sensor nodes and implantable medical devices." (2016). Purdue University, Ph.D. Dissertation.

[57] Chiang, Cheng-Yi, Hong-Hui Chen, Tung-Chien Chen, Chien-Sheng Liu, Yu-Jie Huang, Shey-Shi Lu, Chii-Wann Lin, and Liang-Gee Chen. "Analysis and design of on-sensor ECG processors for realtime detection of VF, VT, and PVC." In 2010 IEEE Workshop On Signal Processing Systems, pp. 42-45. IEEE, 2010.

[58] Chuo, Yindar, Marcin Marzencki, Benny Hung, Camille Jaggernauth, Kouhyar Tavakolian, Philip Lin, and Bozena Kaminska. "Mechanically flexible wireless multisensor platform for human physical activity and vitals monitoring." IEEE transactions on biomedical circuits and systems 4, no. 5 (2010): 281-294.

[59] Dai, Ming, Xueliang Xiao, Xin Chen, Haoming Lin, Wanqing Wu, and Siping Chen. "A low-power and miniaturized electrocardiograph data collection system with smart textile electrodes for monitoring of cardiac function." Australasian physical & engineering sciences in medicine 39, no. 4 (2016): 1029-1040.

[60] Dey, P. S., and N. Kayalvizhi, "ECG System as Smartphone Peripheral," 2019 9th International Conference on Advances in Computing and Communication (ICACC), Kochi, India, 2019, pp. 27-30, doi: 10.1109/ICACC48162.2019.8986187.

[61] Fulford-Jones, Thaddeus R F, Gu-Yeon Wei, and Matt Welsh. "A portable, low-power, wireless two-lead EKG system." In The 26th Annual International Conference of the IEEE Engineering in Medicine and Biology Society, vol. 1, pp. 2141-2144. IEEE, 2004.

[62] Gong, Zhun, and Yaru Ding. "Design and Implementation of Wearable Dynamic Electrocardiograph Real-time Monitoring Terminal." IEEE Access (2019).

[63] Hernandez-Silveira, M., S. S. Ang, T. Mehta, and B. Wangand A. Burdett. "Implementation And Evaluation Of A Physical Activity And Energy Expenditure Algorithm In A Sensium™-Based Body-Worn Device." (2012). DOI: 10.5220/0003786902190223, In Proceedings of the International Conference on Biomedical Electronics and Devices (BIODEVICES-2012), pages 219-223, ISBN: 978-989-8425-91-1

[64] Hsiao, Chun-Chieh, Ren-Guey Lee, Sheng-Chung Tien, Yen-Yi Feng, and Shih-Feng Huang. "Early clinical prognosis for high-risk chest pain patients using smart textiles." Biomedical Engineering: Applications, Basis and Communications 27, no. 06 (2015): 1550057.

[65] Izumi, Shintaro, Hiroshi Kawaguchi, Masahiko Yoshimoto, and Yoshikazu Fujimori. "Normally-off technologies for healthcare appliance." In 2014 19th Asia and South Pacific Design Automation Conference (ASP-DAC), pp. 17-20. IEEE, 2014.

[66] Izumi, Shintaro, Ken Yamashita, Masanao Nakano, Hiroshi Kawaguchi, Hiromitsu Kimura, Kyoji Marumoto, Takaaki Fuchikami et al. "A Wearable Healthcare System With a 13.7 µA Noise Tolerant ECG Processor." IEEE transactions on biomedical circuits and systems 9, no. 5 (2014): 733-742.

[67] Jain, Anshul, Yamini Goyal, and Ajit Patel. "ECG Analysis System with Event Detection based on Daubechies Wavelets." International Journal of Advanced Computer Research (ISSN (print): 2249-7277 ISSN (online): 2277-7970) 3 (2012).

[68] Jha, Pankaj Kumar, and Asudeb Dutta. "Process Aware Analog-Centric Single Lead Ecg Acquisition And Classification CMOS Frontend." PhD diss., Indian institute of technology Hyderabad, 2018.

[69] Kalaskar Radha B., and Bharati Harsoor. "An End-to-End Point of Cardiovascular Body Sensor Network with Cloud Service." Bharati, An End-to-End Point of Cardiovascular Body Sensor Network with Cloud Service (May 17, 2019) (2019).

[70] Khandoker, Ahsan H., and Brian A. Walker. "Designing a Low-Cost ECG Sensor and Monitor: Practical Considerations and Measures." Healthcare Sensor Networks: Challenges Toward Practical Implementation (2016): 339.

[71] Lee, Kyong Ho, and Naveen Verma. "A low-power processor with configurable embedded machine-learning accelerators for high-order and adaptive analysis of medical-sensor signals." IEEE Journal of Solid-State Circuits 48, no. 7 (2013): 1625-1637.

[72] Lee, Seulki, Long Yan, Taehwan Roh, Sunjoo Hong, and Hoi-Jun Yoo. "A 75 µW real-time scalable network controller and a 25 µW ExG sensor IC for compact sleep-monitoring applications." In 2011 IEEE International Solid-State Circuits Conference, pp. 36-38. IEEE, 2011.

[73] Liang, Jifu, Shixiong Li, Ali Nikoofard, and Soumyajit Mandal. "A low-power receiver for simultaneous electrocardiogram and respiration rate detection." In 2016 IEEE international symposium on circuits and systems (ISCAS), pp. 2455-2458. IEEE, 2016.

[74] Lou, Dongdong, Xianxiang Chen, Zhan Zhao, Yundong Xuan, Zhihong Xu, Huan Jin, Xingzu Guo, and Zhen Fang. "A wireless health monitoring system based on android operating system." Ieri Procedia 4 (2013): 208-215.

[75] Majumder, S., L. Chen, O. Marinov, C. Chen, T. Mondal and M. J. Deen, "Noncontact Wearable Wireless ECG Systems for Long-Term Monitoring," in IEEE Reviews in Biomedical Engineering, vol. 11, pp. 306-321, 2018, doi: 10.1109/RBME.2018.2840336.

[76] Meziane, N., J. G. Webster, Mokhtar Attari, and A. J. Nimunkar. "Dry electrodes for electrocardiography." Physiological measurement 34, no. 9 (2013): R47.

[77] Naranjo-Hernández, David, Laura M. Roa, Javier Reina-Tosina, Gerardo Barbarov-Rostan, and Omar Galdámez-Cruz. "Smart device for the determination of heart rate variability in real time." Journal of Sensors 2017 (2017).

[78] Noor, Safwat Mostafa. "Low energy computation methods for implantable cardiac pacemaker workloads." PhD diss., The University of Texas at San Antonio, 2016.

[79] Oweis, R. J., & A. Barhoum (2007) PIC microcontroller-based RF wireless ECG monitoring system, Journal of Medical Engineering & Technology, 31:6, 410-418, DOI: 10.1080/03091900600703560

[80] Ozkan, Haydar, Orhan Ozhan, Yasemin Karadana, Muhammed Gulcu, Samet Macit, and Fasahath Husain. "A Portable Wearable Tele-ECG Monitoring System." IEEE Transactions on Instrumentation and Measurement 69, no. 1 (2019): 173-182.

[81] Rajashree, Radha B K. "Real-Time Ambulatory Monitoring System." (2017). International Research Journal of Engineering and Technology (IRJET) e-ISSN: 2395-0056, Volume: 04 Issue: 05|May-2017

[82] Sankman, Robert L., Ian A. Young, Johanna M. Swan, and Marko Radosavljevic. "Electronic bio monitoring patch." U.S. patent application Ser. No. 13/719,360, filed Jun. 19, 2014.

[83] Toral, Victor, Antonio Garcia, Francisco J. Romero, Diego P. Morales, Encarnación Castillo, Luis Parrilla, Francisco M. Gomez-Campos, Antonio Morillas, and Alejandro Sánchez. "Wearable system for biosignal acquisition and monitoring based on reconfigurable technologies." Sensors 19, no. 7 (2019): 1590.

[84] Valchinov, Emil, Athanasios Antoniou, Konstantinos Rotas, and Nicolas Pallikarakis. "Wearable ECG system for health and sports monitoring." In 2014 4th International Conference on Wireless Mobile Communication and Healthcare-Transforming Healthcare Through Innovations in Mobile and Wireless Technologies (MOBIHEALTH), pp. 63-66. IEEE, 2014.

[85] Wannenburg, Johan, Reza Malekian, and Gerhard P. Hancke. "Wireless capacitive-based ECG sensing for feature extraction and mobile health monitoring." IEEE Sensors Journal 18, no. 14 (2018): 6023-6032.

[86] Wong, A. C. W., D. McDonagh, O. Omeni, C. Nunn, M. Hernandez-Silveira, and A. J. Burdett. "Sensium: An ultra-low-power wireless body sensor network platform: Design & application challenges." In 2009 Annual International Conference of the IEEE Engineering in Medicine and Biology Society, pp. 6576-6579. IEEE, 2009.

[87] Wu, C-C., W-C. Kuo, H-J. Wang, Y-C. Huang, Y-H. Chen, Y-Y. Chou, S-A. Yu, and S-S. Lu. "A pliable and batteryless real-time ECG monitoring system-in-a-patch." In VLSI Design, Automation and Test (VLSI-DAT), pp. 1-4. IEEE, 2015.

[88] Xu, Zhihong, Zhen Fang, Lidong Du, Zhan Zhao, Xianxiang Chen, Diliang Chen, Fangmin Sun, Yangming Qian, Huaiyong Li, and Lili Tian. "A Wearable Multi-parameter Physiological System." In Ubiquitous Information Technologies and Applications, pp. 643-648. Springer, Berlin, Heidelberg, 2014.

[89] Yan, Long, and Hoi-Jun Yoo. "A low-power portable ECG touch sensor with two dry metal contact electrodes." Journal of semiconductor technology and science 10, no. 4 (2010): 300-308.

[90] Yan, Long, Joonsung Bae, Seulki Lee, Binhee Kim, Taehwan Roh, Kiseok Song, and Hoi-Jun Yoo. "A 3.9 mW 25-electrode reconfigured thoracic impedance/ECG SoC with body-channel transponder." In 2010 IEEE International Solid-State Circuits Conference-(ISSCC), pp. 490-491. IEEE, 2010.

[91] Yan, Long, Joonsung Bae, Seulki Lee, Taehwan Roh, Kiseok Song, and Hoi-Jun Yoo. "A 3.9 mW 25-electrode reconfigured sensor for wearable cardiac monitoring system." IEEE Journal of Solid-State Circuits 46, no. 1 (2010): 353-364.

[92] Yoo, Jerald, and Hoi-Jun Yoo. "Emerging low energy wearable body sensor networks using patch sensors for continuous healthcare applications." In 2010 Annual International Conference of the IEEE Engineering in Medicine and Biology, pp. 6381-6384. IEEE, 2010.

[93] Yoo, Jerald, Long Yan, Seulki Lee, Hyejung Kim, and Hoi-Jun Yoo. "A wearable ECG acquisition system with compact planar-fashionable circuit board-based shirt." IEEE Transactions on Information Technology in Biomedicine 13, no. 6 (2009): 897-902.

[94] Yoo, Jerald, Long Yan, Seulki Lee, Yongsang Kim, and Hoi-Jun Yoo. "A 5.2 mW Self-Configured Wearable Body Sensor Network Controller and a 12 µW Wirelessly Powered Sensor for a Continuous Health Monitoring System." IEEE journal of solid-state circuits 45, no. 1 (2009): 178-188.

[95] Yoshimoto, Masahiko, and Shintaro Izumi. "Recent progress of biomedical processor SoC for wearable healthcare application: A review." IEICE Transactions on Electronics 102, no. 4 (2019): 245-259.

[96] Hou, Zhongjie, et al. "A Real-Time QRS Detection Method Based on Phase Portraits and Box-Scoring Calculation." IEEE Sensors Journal 18.9 (2018): 3694-3702.

[97] Farahabadi, Amin, et al. "Detection of QRS complex in electrocardiogram signal based on a combination of hilbert transform, wavelet transform and adaptive thresholding." Biomedical and Health Informatics (BHI), 2012 IEEE-EMBS Int'l Conf. on. IEEE, 2012.

[98] Spinsante, Susanna, Sara Porfiri and Lorenzo Scalise. "Accuracy of Heart Rate Measurements by a Smartwatch in Low Intensity Activities." 2019 IEEE International Symposium on Medical Measurements and Applications (MeMeA) (2019): 1-6.

[99] Pholpoke, Bhirawich, Techapon Songthawornpong, and Woradorn Wattanapanitch. "A Micropower Motion Artifact Estimator for Input Dynamic Range Reduction in Wearable ECG Acquisition Systems." IEEE transactions on biomedical circuits and systems 13, no. 5 (2019): 1021-1035.

[100] Zhao, Luming, Hu Li, Jianping Meng, and Zhou Li. "The recent advances in self-powered medical information sensors." InfoMat 2, no. 1 (2020): 212-234.

[101] Chen, Shuwen, Jiaming Qi, Shicheng Fan, Zheng Qiao, Joo Chuan Yeo, and Chwee Teck Lim. "Flexible Wearable Sensors for Cardiovascular Health Monitoring." Advanced Healthcare Materials (2021): 2100116.

[102] Lin, Qi, Weitao Xu, Guohao Lan, Yesheng Cui, Hong Jia, Wen Hu, Mahbub Hassan, and Aruna Seneviratne. "KEHKey: Kinetic Energy Harvester-based Authentication and Key Generation for Body Area Network." Proceedings of the ACM on Interactive, Mobile, Wearable and Ubiquitous Technologies 4, no. 1 (2020): 1-26.

[103] Kartsch, Victor, Fiorenzo Artoni, Simone Benatti, Silvestro Micera, and Luca Benini. "Using Low-Power, Low-Cost IoT Processors in Clinical Biosignal Research: an In-depth Feasibility Check." In 2020 42nd Annual International Conference of the IEEE Engineering in Medicine & Biology Society (EMBC), pp. 4008-4011. IEEE, 2020.

[104] Tan, Puchuan, Yang Zou, Yubo Fan, and Zhou Li. "Self-powered wearable electronics." Wearable Technologies 1 (2020).

[105] Chatzigiannakis, Ioannis, and Christos Tselios. "Internet of Everything." In Intelligent Computing for Interactive System Design: Statistics, Digital Signal Processing, and Machine Learning in Practice, pp. 21-56. 2021.

[106] Cosoli, Gloria, Susanna Spinsante, Francesco Scardulla, Leonardo D'Acquisto, and Lorenzo Scalise. "Wireless ECG and cardiac monitoring systems: state of the art, available commercial devices and useful electronic components." Measurement (2021): 109243.

[107] Lin, Qiuyang, Shuang Song, Ivan D. Castro, Hui Jiang, Mario Konijnenburg, Roland van Wegberg, Dwaipayan Biswas et al. "Wearable Multiple Modality Bio-Signal Recording and Processing on Chip: A Review." IEEE Sensors Journal 21, no. 2 (2020): 1108-1123.

[108] Kim, Junho, Hyeok Kim, Dongwook Kim, Hun-Jun Park, Kiwon Ban, Seungyoung Ahn, and Sung-Min Park. "A wireless power transfer based implantable ECG monitoring device." Energies 13, no. 4 (2020): 905.

[109] Long, Yan, Yongli Chen, Deyong Xiao, Zheng Li, Tianpeng Hou, and Zhiwei Zhang. "Research on a Bluetooth Low Energy Warning Method." In Journal of Physics: Conference Series, vol. 1631, no. 1, p. 012162. IOP Publishing, 2020.

[110] Christoe, Michael J., Jialuo Han, and Kourosh Kalantar-Zadeh. "Telecommunications and data processing in flexible electronic systems." Advanced Materials Technologies 5, no. 1 (2020): 1900733.

[111] Singh, Mandeep, Gurmohan Singh, Jaspal Singh, and Yadwinder Kumar. "Design and Validation of Wearable Smartphone Based Wireless Cardiac Activity Monitoring Sensor." Wireless Personal Communications (2021): 1-17.

[112] Randazzo, Vincenzo, Jacopo Ferretti, and Eros Pasero. "A wearable smart device to monitor multiple vital parameters—VITAL ECG." Electronics 9, no. 2 (2020): 300.

[113] Bai, Baodan, Yufang Zhao, Xinrong Chen, Yingmin Chen, and Zhangyuan Luo. "A smart portable ECG monitoring system with high precision and low power consumption." Journal of Intelligent & Fuzzy Systems Preprint: 1-11.

[114] Uchiyama, Akira, Shunsuke Saruwatari, Takuya Maekawa, Kazuya Ohara, and Teruo Higashino. "Context Recognition by Wireless Sensing: A Comprehensive Survey." Journal of Information Processing 29 (2021): 46-57.

See U.S. Pat. Nos. ad Pat. App. Nos. 20200161001; 20200139120; 20200121249; 20200107775; 20200000441; 20200000355; 20190387989; 20190366045; 20190350457; 20190336038; 20190320974; 20190290137; 20190261912; 20190261153; 20190259268; 20190254523; 20190246966; 20190239724; 20190223749; 20190214153; 20190213862; 20190151604; 20190147721; 20190040360; 20190008396; 20180368495; 20180317797; 20180279879; 20180247029; 20180199842; 20180146875; 20180055373; 20180050216; 20170354831; 20170344736; 20170340233; 20170333712; 20170266443; 20170265838; 20170231520; 20170225005; 20170215754; 20170215752; 20170135595; 20170055900; 20160359150; 20160331974; 20160302725; 20160287122; 20160262691; 20160249817; 20160246940; 20160206876; 20160193466; 20160183829; 20160074671; 20160067517; 20160067515; 20160029906; 20150359964; 20150351799; 20150351690; 20150335288; 20150234986; 20150202454; 20150141792; 20150141791; 20150105640; 20150094557; 20150073230; 20140358193; 20140343641; 20140328806; 20140303647; 20140213879; 20140163304; 20140148870; 20140148714; 20140094808; 20140068116; 20140046423; 20140046188; 20130237864; 20130231546; 20130184599; 20130150698; 20130096448; 20130072746; 20130053674; 20120302821; 20120165644; 20120109258; 20120083764; 20120053432; 20110265345; 20110160601; 20110046626; 20110046507; 20110040237; 20110028938; 20110021863; 20100298687; 20100222629; 20100211140; 20100204538; 20100168501; 20100160712; 20100115791; 20100056871; 20100036231; 20100005685; 20090318796; 20090318793; 20090234325; 20090234179; 20090227831; 20090227829; 20090210956; 20090130623; 20090037611; 20080306325; 20080281180; 20080263895; 20080249188; 20080234594; 20080004613; 20070190651; 20070149887; 20070144037; 20070123813; 20070009542; 20060276552; 20060264767; 20060224072; 20060156580; 20060099194; 20060041241; 20050283998; 20040138584; 20040134097; 20040123493; 20040006891; 20030212319; 20020157280; 20020023374; 20200160670; 20200126370; 20200118401; 20200118400; 20190363746; 20190341954; 20190182357; 20180316781; 20180085593; 20170034618; 20140276262; 20030199778; 20030032993; 10,537,403; 10,586,623; 10,582,358; 10,573,134; 10,561,842; 10,548,500; 10,537,250; 10,531,813; 10,510,219; 10,485,980; 10,478,623; 10,478,084; 10,441,602; 10,423,193; 10,413,733; 10,405,767; D854,167; U.S. Pat. No. 10,355,730; D852,965; U.S. Pat. No. 10,285,617; 10,285,608; 10,219,714; 10,187,773; 10,178,974; 10,165,355; 10,159,421; 10,159,415; 10,142,822; 10,140,820; 10,124,172; 10,111,643; 10,106,776; 10,049,182; 10,038,992; 9,911,290; 9,907,478; 9,894,471; 9,888,337; 9,867,990; 9,839,363; 9,833,158; 9,814,423; 9,804,635; 9,782,097; 9,775,741; 9,757,584; 9,737,225; 9,717,435; 9,681,814; 9,675,512; 9,649,042; 9,630,004; 9,610,459; 9,579,062; 9,572,499; 9,524,253; 9,463,169; 9,451,975; 9,420,956; 9,403,000; 9,387,338; 9,375,179; 9,351,654; 9,339,641; 9,307,921; 9,254,095; 9,254,092; 9,247,911; 9,220,430; 9,202,360; 9,173,670; 9,089,254; 9,040,101; 9,026,202; 9,022,949; 9,014,778; 9,005,102; 9,002,477; 8,948,854; 8,805,475; 8,761,858; 8,738,112; 8,721,699; 8,700,137; 8,688,189; 8,669,864; 8,636,748; 8,630,633; 8,611,980; 8,571,622; 8,509,882; 8,494,507; 8,480,723; 8,441,356; 8,435,166; 8,430,805; 8,428,683; 8,313,520; 8,301,232; 8,290,577; 8,241,229; 8,075,605; 7,950,971; 7,921,580; 7,877,900; 7,848,799; 7,837,722; 7,824,436; 7,805,849; 7,524,490; 7,337,559; 7,168,186; 7,036,

245; 7,010,352; 6,842,999; 6,615,074; 6,327,795; 5,916,157; 5,658,277; and 5,582,574.

What is claimed is:

1. An electrocardiogram sensor, comprising:
an analog processing component configured to process a signal comprising cardiac electrical activity;
a digitizer configured to create a digital representation of the signal;
a microprocessor, configured to:
receive the digital representation of the signal;
process the digital representation to determine at least one electrocardiographic feature and periods during which the digital representation of the signal represents artifact;
analyze the determined at least one electrocardiographic feature to determine at least heart rate; and
conditionally generate information packets having a plurality of different information types, the information packets having a respective information type conditionally dependent on at least the determined at least one electrocardiographic feature and the determined periods during which the digital representation of the signal represents artifact; and
a wireless communication device, under control of the microprocessor, configured to remain in a non-transmitting low power state without transmitting information packets for the periods representing artifact, and to enter a transmitting high power state for transmission of the conditionally generated information packets containing valid statistics for at least the heart rate, and subsequently revert to the low power state after transmission.

2. The electrocardiogram sensor according to claim 1, further comprising a substrate supporting the microprocessor, a set of electrodes for receiving the signal comprising cardiac electrical activity, and a self-contained power source, configured to power the analog processor, the digitizer, the microprocessor, and the wireless communication device.

3. The electrocardiogram sensor according to claim 2,
wherein the substrate is wearable and has at least two of the set of electrodes formed on the substrate, configured to receive the transdermal bioelectric signals representing the cardiac electrical activity through human skin; and
an adhesive layer configured to adhere the at least two of the set electrodes to the skin.

4. The electrocardiogram sensor according to claim 1, wherein the microprocessor is further configured to determine heart rate variability, and the contingently generated information packets further contain valid statistics for at least the heart rate variability.

5. The electrocardiogram sensor according to claim 4, wherein the microprocessor is configured to:
maintain a data buffer for electrocardiographic data in a memory,
periodically form an information packet from the maintained electrocardiographic data; and
overwrite the contents of the data buffer with subsequent electrocardiographic data.

6. The electrocardiogram sensor according to claim 1, wherein the microprocessor is configured to extract a plurality of electrocardiographic features from the cardiac electrical activity, and transmit at least one of the plurality of electrocardiographic features and a series of samples from the digitizer representing the cardiac electrical activity in the contingently generated information packets.

7. The electrocardiogram sensor according to claim 1, wherein the microprocessor is further configured to determine an electrocardiographic alarm state, and to transmit an alert selectively dependent on the determined electrocardiographic alarm state.

8. The electrocardiogram sensor according to claim 1, wherein the microprocessor is further configured to automatically process the digital representation to determine valid cardiac statistics.

9. The electrocardiogram sensor according to claim 1, wherein the microprocessor is further configured to receive control information through the wireless communication device which determines an energy consumption rate of the electrocardiogram sensor.

10. The electrocardiogram sensor according to claim 1, wherein the microprocessor is configured to analyze the determined at least one electrocardiographic feature to determine at least heart rate by determining occurrence of R waves.

11. The electrocardiogram sensor according to claim 1, wherein the microprocessor is further configured to automatically:
process the digital representation to periodically determine a baseline representing a statistical reference signal level;
store the data representing the baseline in a memory;
determine a leads-off condition of an electrocardiographic electrode; and
redetermine the baseline after the leads off condition has abated.

12. The electrocardiogram sensor according to claim 11, wherein the microprocessor is further configured to automatically process the digital representation with respect to the baseline, to detect an artifact.

13. The electrocardiogram sensor according to claim 1, wherein the microprocessor is further configured to determine occurrence of a cardiac arrhythmia, and to selectively contingently generate the information packets comprising information indicative of the cardiac arrythmia.

14. The electrocardiogram sensor according to claim 11, wherein the microprocessor is further configured to control the wireless communication device to communicate the digital representation subsequent to the determined occurrence of the cardiac arrhythmia, and to control the wireless communication device to communicate a set of parameters characterizing the cardiac electrical activity but not comprising the digital representation prior to the determined occurrence of the cardiac arrhythmia.

15. The electrocardiogram sensor according to claim 1, further comprising a microprocessor implemented biological model of expected cardiac electrical activity, and wherein the periods representing artifact are periods during which the digital representation of the electrocardiographic signal includes unexpected values with respect to the microprocessor implemented biological model.

16. The electrocardiogram sensor according to claim 2,
wherein the substrate comprises a flexible substrate having at least two electrodes adapted for skin contact, configured to receive the transdermal bioelectric signals representing the cardiac electrical activity,
further comprising an adhesive layer configured to adhere with flexible substrate to human skin, without interference with the at least two electrodes making skin contact.

17. The electrocardiogram sensor according to claim 1, wherein the periods representing artifact comprise periods of at least one of noise artifacts, motion artifacts, and electrode non-contact artifacts.

18. A method for operating electrocardiogram sensor, comprising:
processing a signal comprising cardiac electrical activity received from a set of electrodes with an analog signal processing component;
digitizing the processed signal to create a digital representation of the signal;
automatically processing the digital representation to determine at least one electrocardiographic feature and periods during which the digital representation of the signal represents artifact;
analyzing the at least one determined electrocardiographic feature to determine at least a heart rate;
contingently generating information packets having a plurality of different information types, the information packets having a respective information type dependent on at least the determined at least one electrocardiographic feature and the determined periods representing artifact; and
wireless communicating the information packets, under control of a microprocessor, to remain in a non-transmitting low power state without transmitting information packets for the periods representing artifact, and to enter a transmitting high power state for transmission of the contingently generated information packets containing valid statistics for at least the heart rate, and subsequently revert to the low power state after transmission.

19. The method of claim 18,
wherein the wireless communicating comprises transmitting a radio frequency signal through an antenna formed on a flexible substrate supporting the microprocessor and at least two of the set of electrodes configured to acquire an electrocardiographic signal through human skin;
further comprising:
receiving a command through the antenna to control the microprocessor;
buffering electrocardiographic data with the microprocessor in a memory,
periodically forming an information packet from the buffered electrocardiographic data; and
overwriting the buffered electrocardiographic data after transmission.

20. The method according to claim 18, further comprising:
extracting a plurality of electrocardiographic features from the cardiac electrical activity; and
transmitting at least one of the plurality of electrocardiographic features and a series of samples from the digitizer in the contingently generated information packets selectively in dependence on said automatic processing.

21. The method according to claim 18, further comprising and at least one of:
determining an electrocardiographic alarm state based on a periodically determined baseline representing a statistical reference signal level and said automatic processing selectively during periods without artifact, and communicating an alert selectively in dependence on the determined electrocardiographic alarm state; and
automatically processing the digital representation to determine valid cardiac statistics.

22. A non-transitory computer readable medium for controlling at least one microprocessor operating a electrocardiogram sensor, comprising:
instructions for digitizing a signal from a set of electrodes to create a digital representation of the signal;
instructions for processing the digital representation to determine at least one electrocardiographic feature and periods during which the digital representation of the signal represents artifact;
instructions for analyzing the at least one determined electrocardiographic feature to determine at least heart rate;
instructions for contingently generating information packets having a plurality of different information types, the information packets having a respective information type dependent on at least the determined at least one electrocardiographic feature and the determined periods representing artifact; and
instructions for communicating the information packets, to remain in a non-transmitting state without transmitting information packets for the periods representing artifact, and to enter a transmitting state for transmission of the contingently generated information packets containing valid statistics for at least the heart rate, and subsequently revert to the non-transmitting state after transmission.

* * * * *